(12) United States Patent
Higuchi et al.

(10) Patent No.: US 7,923,530 B2
(45) Date of Patent: Apr. 12, 2011

(54) ELECTROCHROMIC POLYMER MATERIAL

(75) Inventors: Masayoshi Higuchi, Tsukuba (JP); Yuhki Ohtsuka, Tsukuba (JP); Akari Hayashi, Tsukuba (JP); Dirk G. Kurth, Tsukuba (JP)

(73) Assignee: National Institute for Materials Science, Tsukuba-Shi, Ibaraki (JP)

( * ) Notice: Subject to any disclaimer, the term of this patent is extended or adjusted under 35 U.S.C. 154(b) by 135 days.

(21) Appl. No.: 12/084,047

(22) PCT Filed: May 9, 2006

(86) PCT No.: PCT/JP2006/309619
§ 371 (c)(1),
(2), (4) Date: Apr. 24, 2008

(87) PCT Pub. No.: WO2007/049371
PCT Pub. Date: May 3, 2007

(65) Prior Publication Data
US 2009/0270589 A1    Oct. 29, 2009

(30) Foreign Application Priority Data

Oct. 24, 2005 (JP) ................. 2005-308290
Oct. 24, 2005 (JP) ................. 2005-308291

(51) Int. Cl.
*C08G 73/06* (2006.01)
(52) U.S. Cl. ......... 528/423; 546/257; 359/265; 359/321
(58) Field of Classification Search .......... 528/423; 546/257; 359/265, 321
See application file for complete search history.

(56) References Cited

U.S. PATENT DOCUMENTS
2004/0061121 A1 * 4/2004 Uchida ............... 257/82

FOREIGN PATENT DOCUMENTS
| JP | 2003-336043 | 11/2003 |
| JP | 2004-020928 | 1/2004 |
| JP | 2005-200384 | 7/2005 |
| JP | 2006-016577 | 1/2006 |

OTHER PUBLICATIONS

Yu et al. (Adv. Mater. 2003, 15, 19, 1643-1647).*
Newkome et al. (Chem Eur. J. 2004, 10,1493-1500).*
Newkome et al. (Chem Eur. J. 2002, 8, 2946-2954).*

* cited by examiner

*Primary Examiner* — Randy Gulakowski
*Assistant Examiner* — Shane Fang
(74) *Attorney, Agent, or Firm* — Manabu Kanesaka

(57) ABSTRACT

Provided are (1) a terpyridine monomer that has a strong ability to coordinate with metal atoms, and (2) a polymer material that can be readily switched between a colored state and a colorless state by controlling the electrical potential applied to it and that can be processed.

A bis-terpyridine monomer of a first invention comprises a first terpyridyl substituent (A), a second terpyridyl substituent (B), and a spacer that contains at least one benzene ring and links the substituents (A) and (B).

A polymer material of a second invention comprises a bis-terpyridine derivative derived from the monomer according to the first invention, a metal ion and a counter anion, or comprise first to Nth bis-terpyridine derivatives (N is an integer of 2 or greater), first to Nth metal ions (N is an integer of 2 or greater) and first to Nth counter anions (N is an integer of 2 or greater).

2 Claims, 11 Drawing Sheets

Reduced state ⇔ Oxidized state

ELECTROCHROMIC POLYMER MATERIAL

TECHNICAL FIELD

The present invention relates to an electrochromic polymer material that can be readily switched between a colored state and a colorless state by controlling the electrical potential applied to it (Inventions related to this polymer material are referred to as a "second group of invention," hereinafter.)

BACKGROUND ART

In recent years, functional materials with novel properties have been intensively studied. In particular, organic polymers combined with metals are expected to provide new optical, electronic, magnetic, catalytic and various other functions. Such organic polymer-metal composite materials are finding many applications in light-emitting devices, energy-converting materials, drug delivery, sensors, high-performance catalysts, solar batteries and other technical fields.

Organic polymers are soft materials that have spaghetti-like molecular structures with an extremely high degree of freedom. Since organic polymers have a distribution of molecular weights, composites of organic polymers and metals are generally provided in the form of mere statistical mixtures. Thus, coordination polymers, organic polymers that can coordinate with metals, are needed to obtain organic polymer-metal composite materials that exhibit novel useful functions. A technique using bipyridyl derivatives as such coordination polymers is known (See, for example, Patent Document 1).

Light modulation devices, display devices and other optical devices using electrochromic materials have also become the subjects of intensive studies, recently. Such electrochromic materials include inorganic materials, such as tungsten oxide, organic materials, such as viologens, and conductive polymer materials.

It is desirable that these electrochromic materials, when used in light modulation devices, display devices and other optical devices, can be readily switched between the colored state and the colorless state. Although inorganic materials and organic materials can achieve favorable colorless state (transparency), their colored state is undesirable. Conductive polymer materials, on the other hand, can achieve desirable colored state, but their colorless state (transparency) is undesirable. This is because the conductivity of the conductive polymer materials results from the π-electron conjugated system. Non-doped conductive polymer materials thus absorb significant amounts of light and exhibit colors such as dark yellow, red, green and deep blue.

An electrochromic display device technology has been developed that uses a conductive polymer material that has overcome the problem of the undesirable colorless state (See, Patent Document 2). The electrochromic display device used in this technology comprises a first transparent electrode, a graft conductive polymer layer arranged in contact with the first transparent electrode, an electrolyte layer arranged in contact with the graft conductive polymer layer, and a second electrode with which the first transparent electrode sandwiches the graft conductive polymer layer and the electrolyte layer. The graft conductive polymer layer is formed of a conductive polymer backbone linked to a conjugated molecular pendant via a metal or a metal ion.

The conjugated molecular pendant causes the conductive polymer material to change its unique state of π-electron bonding or π-π* transition energy. This in turn causes the light absorption band of the conductive polymer material to shift to a shorter or longer wavelength range. As a result, the light absorption in the visible range is decreased to an unnoticeable degree and the conductive polymer material becomes transparent.

REFERENCE DOCUMENT

Patent Document 1: JP-A-2005-200384
Patent Document 2: JP-A-2004-20928

DISCLOSURE OF THE INVENTION

Problem to be Solved by the Invention

Patent Document 1 describes an organic polymer-metal composite material which is a polymer in which monomer units are linked by metal atoms. In this polymer, the binding between the metal atoms and the bipyridyl derivative may weaken when the valency of the metal atoms changes or the surrounding environment, such as acidity, changes. As a result, the polymer may break down. Thus, there is a need for a coordination polymer that has a strong ability to coordinate with metal atoms.

As opposed to the organic polymer-metal composite material described in Patent Document 1, a polymer in which the polymer backbone encloses metal atoms is expected to not only have increased strength, but also have increased interaction with the metal atoms.

Accordingly, (i) an object of the first group of the present invention is to provide a terpyridine monomer suitable for the synthesis of a polymer that can strongly coordinate with metals, as well as a process for producing the monomer.

The graft conductive polymer layer described in Patent Document 2 is synthesized by the electrolytic polymerization of a monomer. Once synthesized, however, this graft conductive polymer layer is difficult to be re-processed. Thus, there is a need for an electrochromic polymer material that can be readily processed.

Accordingly, (ii) an object of the second group of the present invention is to provide a polymer material that can be readily switched between a colored state and a colorless state by controlling the electrical potential applied to it and that can be readily processed, as well as an electrochromic device using such a polymer material.

Means for Solving the Problem (i) The object of the first group of the present invention is achieved by the following features (1) through (11):

(1) A bis-terpyridine monomer, comprising a first terpyridyl substituent (A), a second terpyridyl substituent (B) and a spacer that contains at least one benzene ring and links the substituents (A) and (B), the bis-terpyridine monomer being represented by the following formula (10):

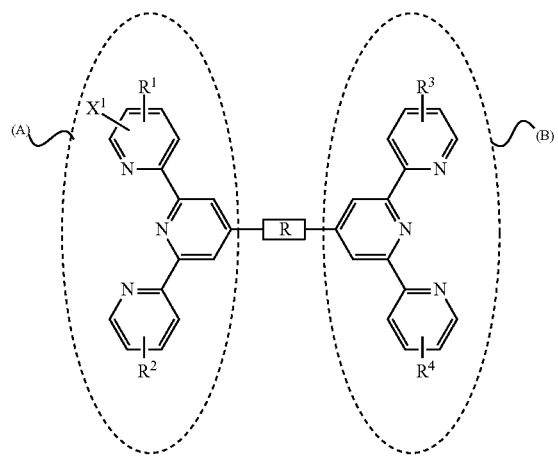

(10)

where $X^1$ is a halogen; and $R^1$, $R^2$, $R^3$ and $R^4$ are each independently a hydrogen atom, an aryl group or an alkyl group.

(2) The bis-terpyridine monomer, wherein the second terpyridyl substituent (B) in the above formula (10) further includes a halogen $X^2$, the bis-terpyridine monomer being represented by the following formula (11):

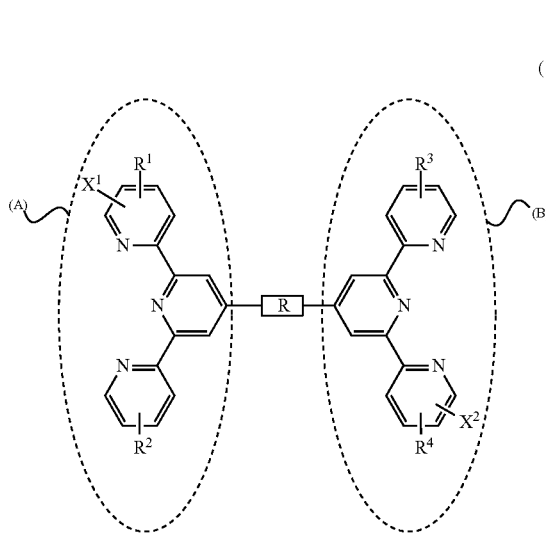

(11)

where $X^2$ is a halogen that may or may not be identical to or different from $X^1$.

(3) The bis-terpyridine monomer, wherein the first terpyridyl substituent (A) in the above formula (11) further includes a halogen $X^3$, the bis-terpyridine monomer being represented by the following formula (12):

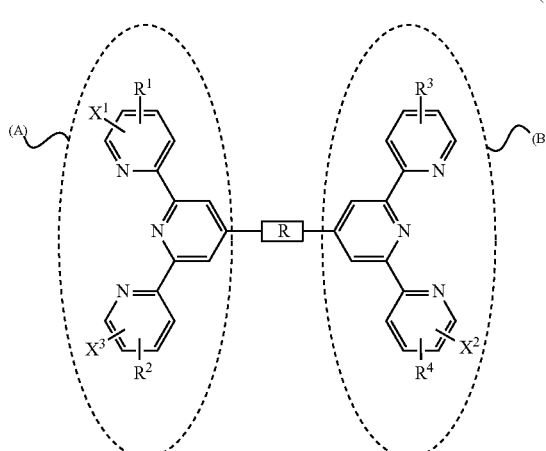

(12)

where $X^3$ is a halogen that may or may not be identical to or different from $X^1$ and/or $X^2$.

(4) The bis-terpyridine monomer, wherein the second terpyridyl substituent (B) in the above formula (12) further includes a halogen $X^4$, the bis-terpyridine monomer being represented by the following formula (13):

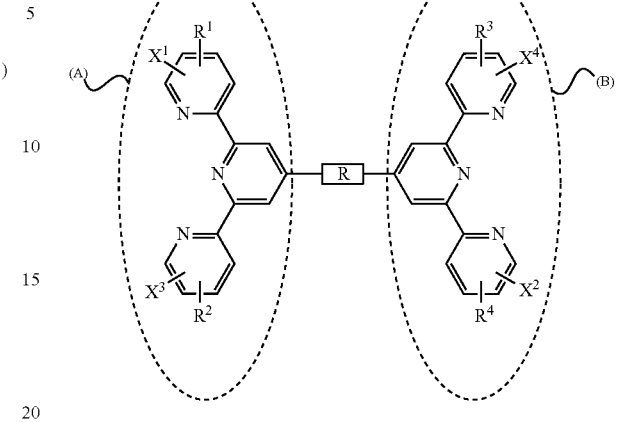

(13)

where $X^4$ is a halogen that may be identical to or different from $X^1$, $X^2$ and/or $X^3$.

(5) The spacer R in each of the above formulas may be selected from the group consisting of the following formulas (3) through (6):

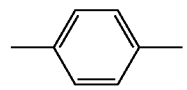

(3)

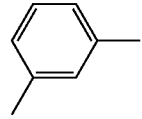

(4)

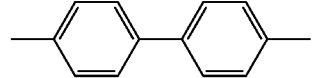

(5)

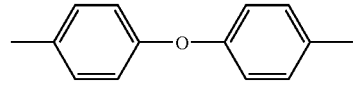

(6)

(6) The $X^1$ in each of the above formulas may be positioned adjacent to the nitrogen atom of the corresponding terminal pyridine.

(7) The $X^1$ and $X^2$ in each of the above formulas may be each positioned adjacent to the nitrogen atom of each corresponding terminal pyridine.

(8) The $X^1$, $X^2$ and $X^3$ in each of the above formulas may be each positioned adjacent to the nitrogen atom of each corresponding terminal pyridine.

(9) The $X^1$, $X^2$, $X^3$ and $X^4$ in each of the above formulas may be each positioned adjacent to the nitrogen atom of each corresponding terminal pyridine.

(10) A process for producing a bis-terpyridine monomer, comprising the steps of:

refluxing a 2-acetylpyridine derivative of the formula (7) and a 2-acetylpyridine derivative of the formula (14) with iodine and pyridine;

reacting an aryldialdehyde derivative of the formula (15) with 2 equivalents of at least one 2-acetylpyridine derivative selected from the group represented by the formula (16) in an aqueous alkaline solution; and refluxing the reaction product of the refluxing step and the reaction product of the reacting step with ammonium acetate and methanol:

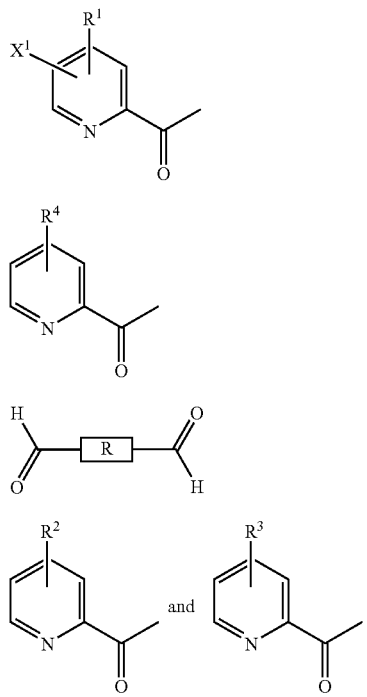

(7)

(14)

(15)

(16)

where $X^1$ is a halogen; $R^1$, $R^2$, $R^3$ and/or $R^4$ are each independently a hydrogen atom, an aryl group or an alkyl group; and R is a spacer containing at least one benzene ring.

(11) The process according to (10), wherein the spacer R is selected from the group consisting of the following formulas (3) through (6):

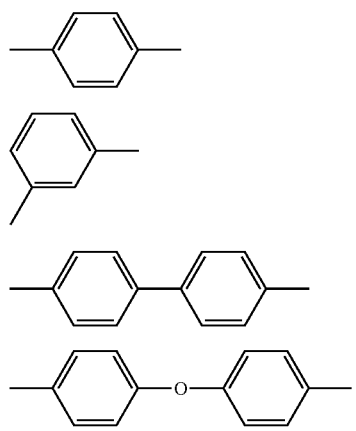

(3)

(4)

(5)

(6)

(ii) The object of the second group of the present invention is achieved by the following features (12) through (22):

(12) An electrochromic polymer material according to the present invention, including a bis-terpyridine derivative, a metal ion and a counter ion, the electrochromic polymer material being represented by the following formula (22):

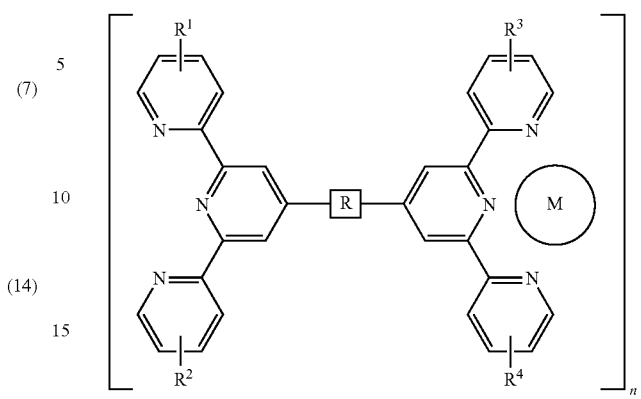

(22)

where M is the metal ion; R is a spacer that contains a carbon atom or a hydrogen atom, or directly links the terpyridyl groups to each other; $R^1$, $R^2$, $R^3$ and $R^4$ are each independently a hydrogen atom, an aryl group or an alkyl group; and n is an integer of 2 or greater indicating the degree of polymerization.

(13) An electrochromic polymer material according to the present invention, including first to Nth bis-terpyridine derivatives (N is an integer of 2 or greater), first to Nth metal ions (N is an integer of 2 or greater) and first to Nth counter anions (N is an integer of 2 or greater), the electrochromic polymer material being represented by the following formula (23):

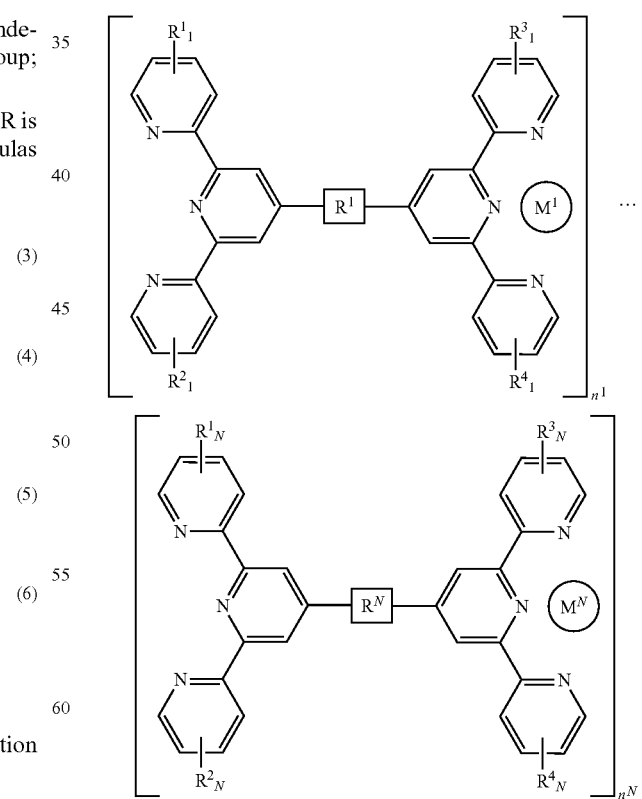

(23)

where $M^1$, ..., $M^N$ are first to Nth different metal ions, respectively (N is an integer of 2 or greater); $R^1$, ..., $R^N$ are each independently a spacer that contains a carbon atom or a hydrogen atom, or directly links corresponding terpyridyl groups to each other (N is an integer of 2 or greater); $R^1_1, \ldots, R^1_N, R^2_1, \ldots, R^2_N, R^3_1, \ldots, R^3_N, R^4_1, \ldots, R^4_N$ are each independently a hydrogen atom, an aryl group or an alkyl group (N is an integer of 2 or greater); $n^1, \ldots, n^N$ are each an integer of 2 or greater indicating the degree of polymerization; and the first to Nth counter anions are identical to, different from, or partly equal to one another.

(14) The first to Nth metal ions may be independently selected from the group consisting of iron ion, cobalt ion, nickel ion and zinc ion.

(15) A process for producing the polymer material according to (12), comprising the step of refluxing a bis-terpyridine derivative of the formula (24) and a metal salt in acetic acid and methanol:

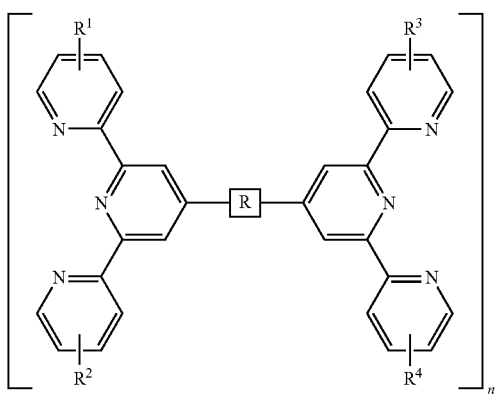

(24)

where R is a spacer that contains a carbon atom or a hydrogen atom, or directly links the terpyridyl groups to each other; $R^1$, $R^2$, $R^3$ and $R^4$ are each independently a hydrogen atom, an aryl group or an alkyl group; and n is an integer of 2 or greater indicating the degree of polymerization.

(16) A process for producing the polymer material according to (13), comprising the steps of: refluxing each of the first to Nth bis-terpyridine derivatives of the formula (25) (N is an integer of 2 or greater) and each of the first to Nth metal salts (N is an integer of 2 or greater) in acetic acid and methanol; and mixing together first to Nth reaction products obtained in the refluxing step (N is an integer of 2 or greater):

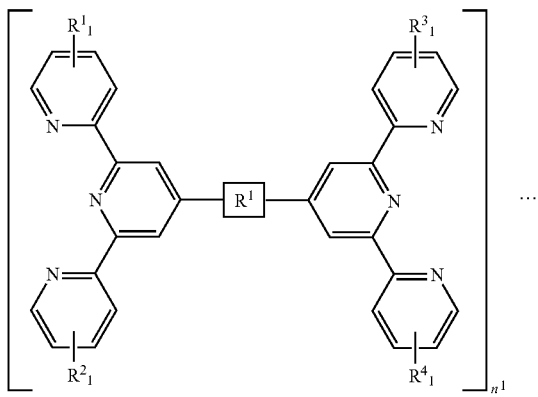

(25)

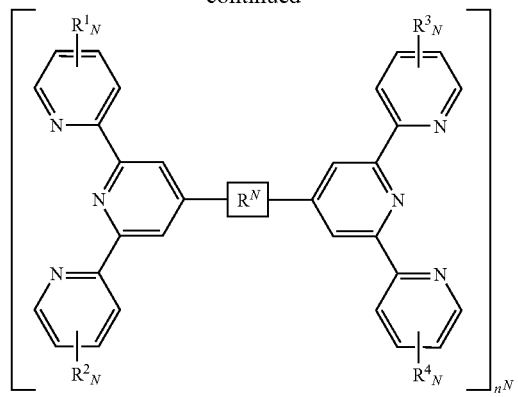

where $R^1, \ldots, R^N$ are each independently a spacer that contains a carbon atom or a hydrogen atom, or directly links corresponding terpyridyl groups to each other (N is an integer of 2 or greater); $R^1_1, \ldots, R^1_N, R^2_1, \ldots, R^2_N, R^3_1, \ldots, R^3_N, R^4_1, \ldots, R^4_N$ are each independently a hydrogen atom, an aryl group or an alkyl group (N is an integer of 2 or greater); and $n^1, \ldots, n^N$, are each an integer of 2 or greater indicating the degree of polymerization.

(17) The process according to (16), wherein the first to Nth metal salts each include a combination of a metal ion selected from the group consisting of iron ion, cobalt ion, nickel ion and zinc ion and a counter anion selected from the group consisting of acetate ion, tetrafluoroborate ion, polyoxometalate and combinations thereof.

(18) The process according to (16), wherein the spacers $R^1, \ldots, R^N$ are each independently an aryl group or an alkyl group.

(19) The process according to (18), wherein the aryl group or alkyl group further contains an oxygen atom or an sulfur atom.

(20) The process according to (18), wherein the aryl group is selected from the group consisting of the following formulas (3) through (6):

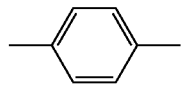

(3)

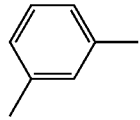

(4)

(5)

(6)

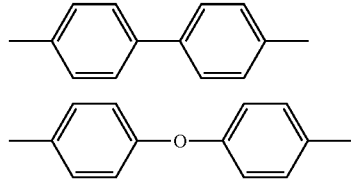

(21) An electrochromic device, comprising a first transparent electrode substrate, a second transparent electrode substrate, and the polymer material according to (12) above arranged between the first transparent electrode substrate and the second transparent electrode substrate.

(22) An electrochromic device, comprising a first transparent electrode substrate, a second transparent electrode substrate, and the polymer material according to (13) or (14) above arranged between the first transparent electrode substrate and the second transparent electrode substrate.

ADVANTAGES OF THE INVENTION

The bis-terpyridine monomer according to the first group of the present invention includes halogens $X^1$ and $X^4$ at specific positions. Such halogens are readily substituted with other substituents. Thus, the monomer can be used to synthesize derivatives having various substituents. Furthermore, the monomer can readily undergo condensation to form polymers that have strong ability to coordinate with metals, the ability that has never been achieved by conventional polymer materials.

In the polymer material derived from the monomer according to the second group of the present invention, electrical charge can move between the metal ion M and the bis-terpyridine derivative, a ligand. Thus, by controlling the electrical potential applied to the polymer material, the metal ion will readily change its valency, causing the polymer material to switch from its colored state to an ideal transparent state. In addition, the polymer material can achieve a desired color by using different combinations of metal ions and ligand, or by using different combinations of metal ions and counter anions. Furthermore, the polymer material of the present invention is soluble in various solvents and can therefore be processed after its synthesis.

EXPLANATION OF REFERENCE SYMBOLS

Figure 1:
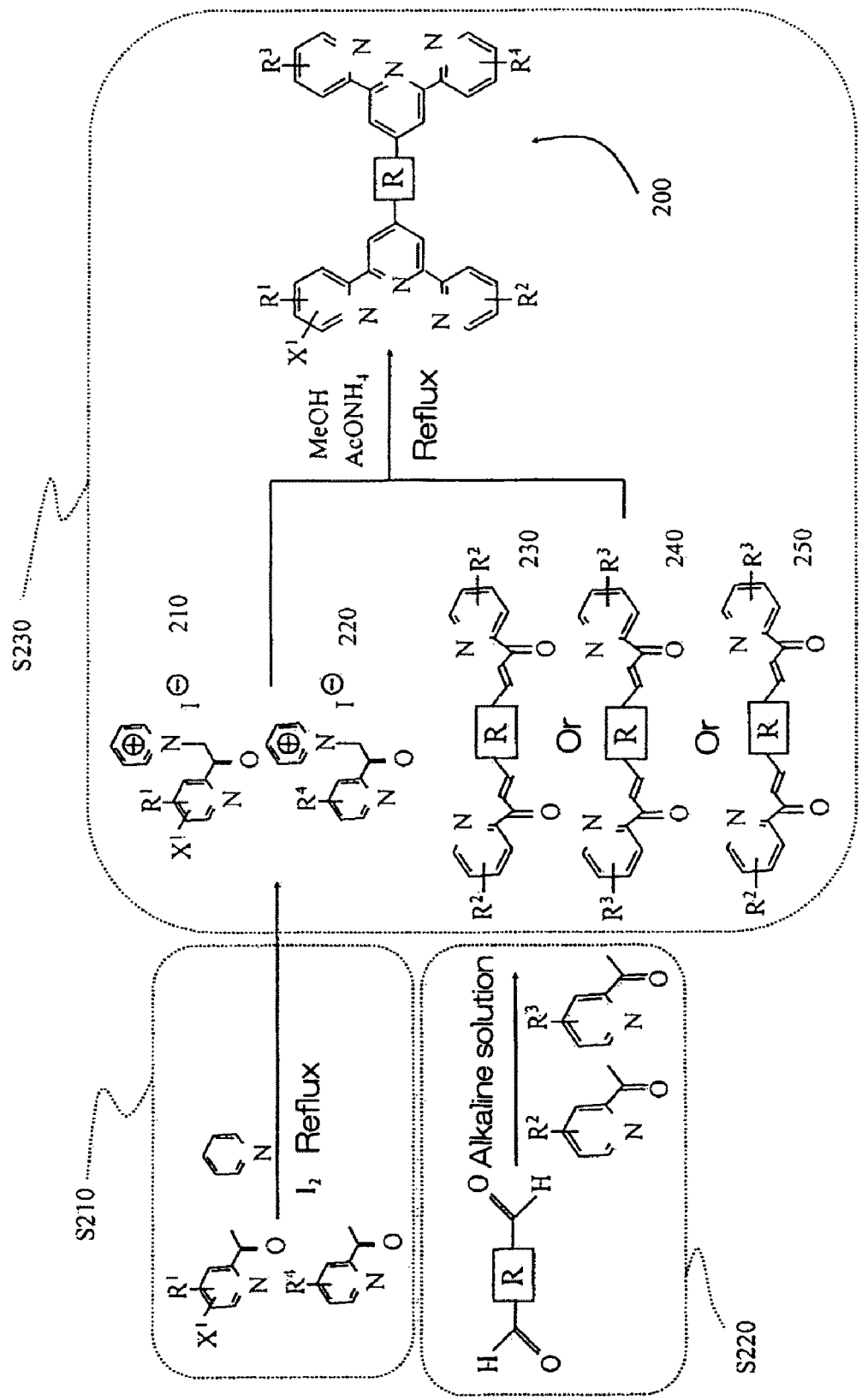
FIG. 1 is a diagram showing a production process of a bis-terpyridine monomer.

300: electrochromic device
310: first transparent electrode
320: polymer material
330: second transparent electrode
340: polymer solid electrolyte

BEST MODE FOR CARRYING OUT THE INVENTION

Several embodiments of the first group of the present invention will now be described with reference to FIGS. 1 and 2.

Embodiment 1

Bis-terpyridine monomers of the present invention are represented by the following formula (10):

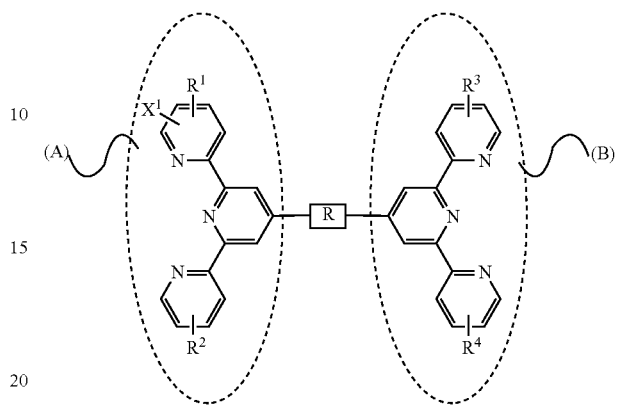

(10)

For comparison, terpyridine monomers are shown below by the formulas (1) and (2):

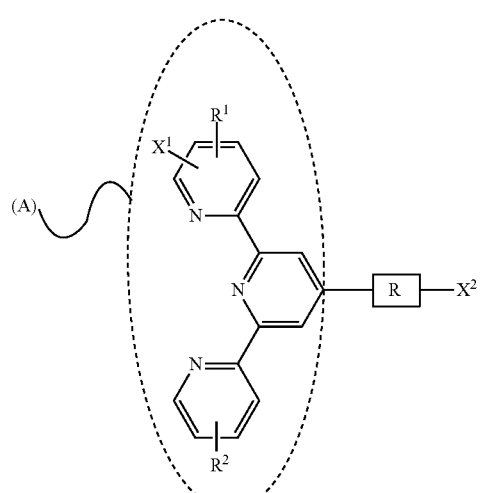

(1)

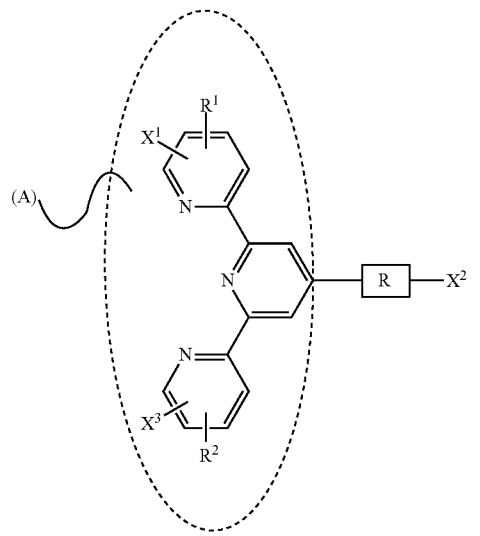

(2)

(1) A bis-terpyridine monomer includes a first terpyridyl substituent (A), a second terpyridyl substituent (B) and a spacer R that links the first terpyridyl substituent (A) and the second terpyridyl substituent (B).

$X^1$ in the first terpyridyl substituent (A) is a halogen, which is preferably bromine, chlorine or iodine, and more preferably bromine. $X^1$ provides the bis-terpyridine monomer with high reactivity. While $X^1$ may be positioned at any position of the terminal pyridine that contains $X^1$, it is preferably positioned adjacent to the nitrogen atom of the terminal pyridine.

$R^1$, $R^2$, $R^3$ and $R^4$ are each independently a hydrogen atom, an aryl group or an alkyl group, Examples include, but are not limited to, methyl group, ethyl group, n-butyl group, t-butyl group, phenyl group and tolyl group. The aryl group or alkyl group may have additional substituents, including alkyl groups, such as methyl group, ethyl group and hexyl group, alkoxy groups, such as methoxy group and butoxy group, and halogen groups, such as chlorine and bromine.

The spacer R includes at least one benzene ring and may be an aryl group or an alkyl group. The spacer R is preferably selected from the group consisting of the formulas (3) through (6) shown below. The spacer R serves to raise the breakdown point (melting point) and thus improve the temperature resistance of the resulting terpyridine monomer. The spacers shown below are each a conjugated aryl group and can readily donate or accept electrons. Terpyridine monomers containing these aryl groups are useful as electronic materials. Also, these aryl groups have more structurally defined skeletons than alkyl groups and therefore allow control of the orientation of terpyridine monomers. Thus, the aryl groups are more advantageous in designing materials than alkyl groups.

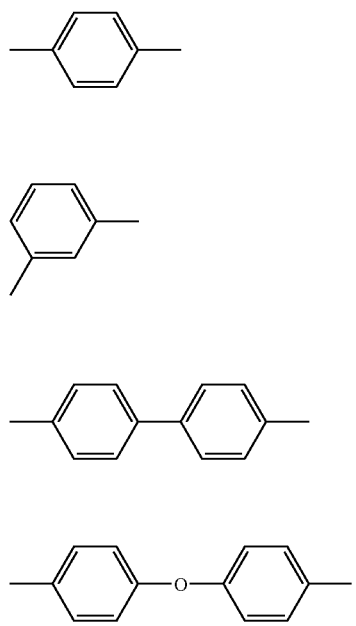

(3)

(4)

(5)

(6)

The second terpyridyl substituent (B) in the bis-terpyridine monomer shown by the formula (10) may contain an additional halogen $X^2$, as shown by the following formula (11)

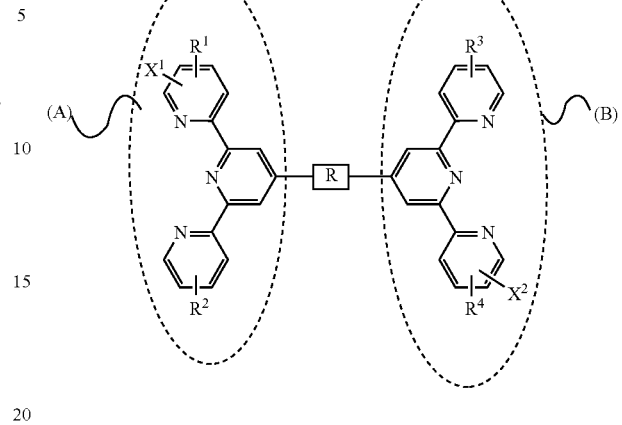

(11)

The additional halogen $X^2$ is bromine, chlorine or iodine, and most preferably bromine. It may or may not be identical to $X^1$. While $X^2$ may be positioned at any position of the terminal pyridine that contains $X^2$, it is preferably positioned adjacent to the nitrogen atom of the terminal pyridine. This allows the bis-terpyridine monomer to be condensed to form a straight-chained polymer.

The first terpyridyl substituent (A) in the bis-terpyridine monomer shown by the formula (11) may contain an additional halogen $X^3$, as shown by the following formula (12):

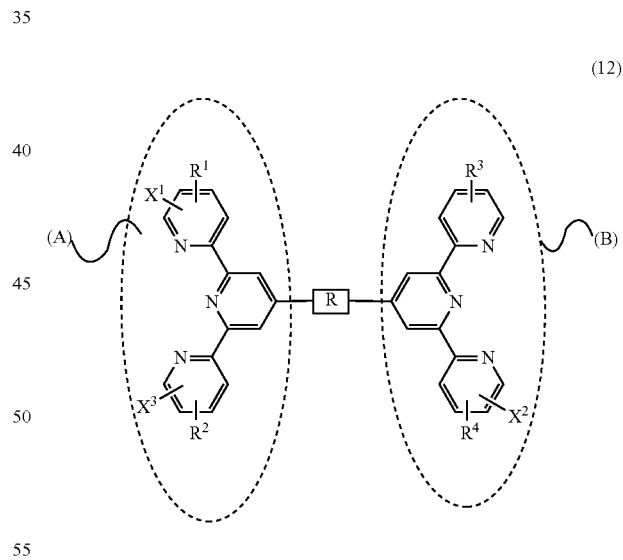

(12)

The additional halogen $X^3$ is bromine, chlorine or iodine, and most preferably bromine. It may or may not be identical to $X^1$ and/or $X^2$. While $X^3$ may be positioned at any position of the terminal pyridine that contains $X^3$, it is preferably positioned adjacent to the nitrogen atom of the terminal pyridine. This allows the bis-terpyridine monomer to be condensed to form a straight-chained polymer.

The second terpyridyl substituent (B) in the bis-terpyridine monomer shown by the formula (12) may contain an additional halogen $X^4$, as shown by the following formula (13):

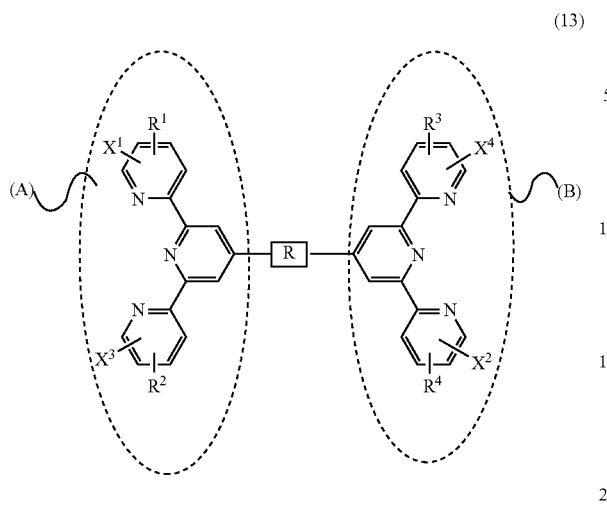

(13)

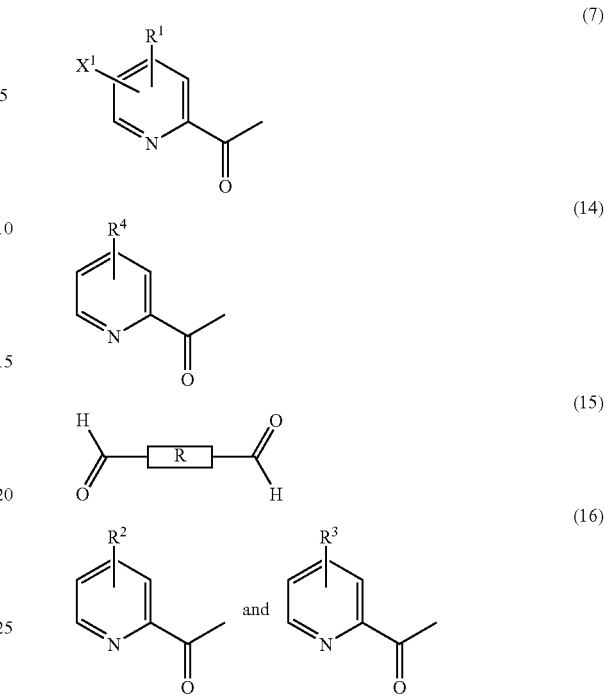

(7)

(14)

(15)

(16)

The additional halogen $X^4$ is bromine, chlorine or iodine, and most preferably bromine. It may or may not be identical to $X^1$, $X^2$ and/or $X^3$. While $X^4$ may be positioned at any position of the terminal pyridine that contains $X^4$, it is preferably positioned adjacent to the nitrogen atom of the terminal pyridine. This allows the bis-terpyridine monomer to be condensed to form a straight-chained polymer.

No previous studies have suggested the bis-terpyridine monomers shown by the formulas (10) through (13) that include the halogens or substituents shown by $X^1$ through $X^4$ that pose a hindrance to the coordination of metal atoms to the terpyridine group. Nor have any studies anticipated polymers that enclose metal atoms, which will be described later in is Embodiment 3. The bis-terpyridine monomers of Embodiment 1, which include two terpyridyl groups, can enclose more metal atoms than the terpyridine monomers that include only one terpyridyl group, which are shown as reference in the formula (1). Thus, the resulting polymer is expected to have increased interaction with the metal atoms, making the polymer applicable to novel devices.

A process for producing the bis-terpyridine monomer of the formula (10) will now be described.

The process for producing the bis-terpyridine monomer is shown in FIG. 1.

The process is described step by step in the following.

Step S210: A 2-acetylpyridine derivative of the formula (7) and a 2-acetylpyridine derivative of the formula (14) are refluxed with iodine and pyridine. This gives a product 210 and a product 220, each a pyrimidium salt.

Step S220: An aryldialdehyde derivative of the formula (15) is reacted with at least one 2-acetylpyridine derivative selected from the group represented by the formula (16), in an alkaline solution. The alkaline solution can enolize the 2-acetylpyridine derivative. The reaction can be carried out by stirring the reaction mixture for at least 24 hours at room temperature. Specifically, the aryldialdehyde derivative is reacted with 2 equivalents of the 2-acetylpyridine derivative. This step gives a product 230, a product 240 or a product 250.

Step S230: The products obtained in Step S210 and Step S220 are refluxed in ammonium acetate and methanol. The products 210 and 220 react with one of the products 230 through 250 to form a bis-terpyridine monomer 200.

In this process, $X^1$ is a halogen, preferably bromine, chlorine or iodine, and most preferably bromine. While $X^1$ may be positioned at any position of the terminal pyridine that contains $X^1$, it is preferably positioned adjacent to the nitrogen atom of the terminal pyridine.

The 2-acetylpyridine derivative of the formula (14) may contain an additional halogen $X^2$. The halogen $X^2$ may or may not be identical to $X^1$ and is preferably bromine. While $X^2$ may be positioned at any position of the terminal pyridine that contains $X^2$, it is preferably positioned adjacent to the nitrogen atom of the terminal pyridine. $X^1$ and $X^2$ are horizontally arranged in the final product 200 obtained in Step 230.

Likewise, the 2-acetylpyridine derivatives of the formula (16) may each contain additional halogens $X^3$ and/or $X^4$. The halogens $X^1$, $X^2$, $X^3$ and $X^4$ may be identical to different from, or partly equal to one another and are each preferably bromine. While halogens $X^3$ and $X^4$ may be positioned at any position of the pyridines that contain them, they are preferably positioned adjacent to the nitrogen atom of the pyridines. All of the halogens are horizontally arranged in the final product 200.

The bis-terpyridine monomer of the present invention, which includes halogens in at least one of its two terpyridine groups, can be used to synthesize not only coordination polymers with metal atoms, but also polymers in which the polymer backbone can enclose metal atoms.

Embodiment 2

Applications of the monomer obtained in Embodiment 1 will now be described.

The monomer obtained in Embodiment 1 can be used to make a bis-type polymer shown by the formula (19) below. In the formula (19), n is an integer of 2 or greater. For comparison, a terpyridyl polymer (18) derived from the formula (1) is shown together as a reference example.

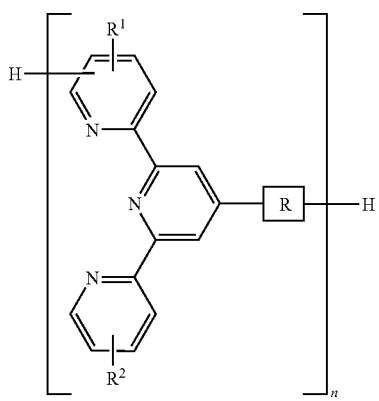

(18)

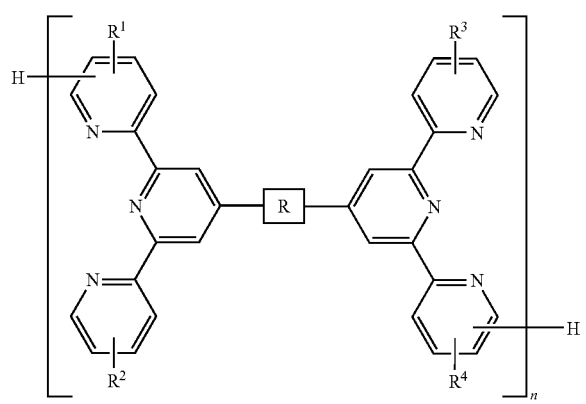

(19)

The polymer of the formula (19) and the polymer of the formula (18) of the reference example are obtained by the condensation of the monomer obtained in Embodiment 1 in the presence of a nickel catalyst or a copper catalyst. The nickel catalyst may be a mixture of bis(1,5-cyclooctadiene) nickel and 2,2'-bipyridyl or tetrakis(triphenylphosphine) nickel. The copper catalyst may be a copper powder.

The condensation reaction can be carried out by dissolving the monomer in a solvent (preferably an organic solvent) and leaving the solution in an atmosphere of inactive gas, such as nitrogen and argon. The solution may be dehydrated or deaerated. While the reaction can be carried out at any suitable temperature, it proceeds effectively at 50° C. to 100° C.

Figure 2:
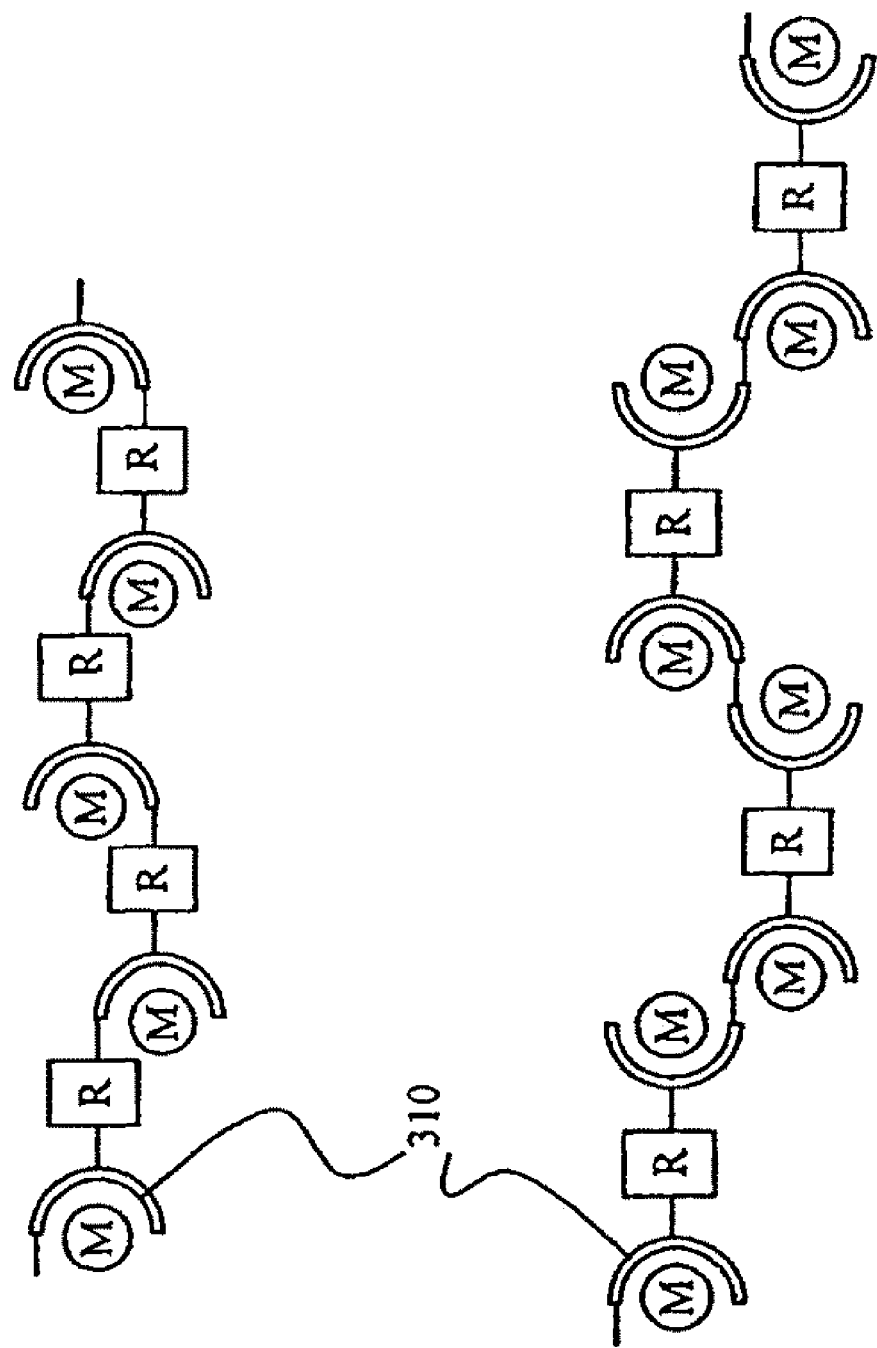
FIG. 2 is a schematic diagram of an organic polymer-metal composite material according to the present invention.

FIG. 2 schematically shows an organic polymer-metal composite material according to the present invention.

FIG. 2(B) shows the composite material of the invention in which the polymer of the formula (19) is coordinated with metal atoms M and FIG. 2(A) (reference example) shows a composite material in which the polymer of the formula (18) is coordinated with metal atoms M.

As shown in FIGS. 2(B) and (A), the polymers shown by the formulas (19) and (18) can enclose the metal atoms M in their terpyridyl moieties 310. The metal atoms enclosed by the polymer backbone do not cause the breakdown of the polymer. In particular, when the spacers are aryl groups described in Embodiments 1 and 2, they can readily donate or accept electrons and allow control of the orientation of the polymer.

The metal atoms have their own electrochemical, spectroscopic and electromagnetic characteristics. These characteristics are affected by the polymer shown by the formula (19) or (18) and can therefore be controlled by introducing proper substituents into the polymer. When moieties having electrochemical, spectroscopic and electromagnetic characteristics are introduced into the polymer of the formula (19), the metal atoms coordinated with the polymer will interact with these moieties. Thus, the characteristics resulting from the polymer may also be controlled by the introduction of such moieties.

The above-described polymers may be used as materials to make organic substrates to deposit metal materials. Such organometallic composite polymer materials have novel characteristics and can be used in light-emitting devices, light-emitting devices, energy-converting materials, drug delivery, sensors, high-performance catalysts, solar batteries and other technical fields. The monomers described in Embodiment 1 and Embodiment 2 may be used as starting materials. In such a case, they may be used in any form and structure and may be copolymerized with other polymers. The monomers may also be mixed with fillers and other materials and shaped into shaped articles.

While examples of the bis-terpyridine monomer of the present invention will now be described in the following, it should be appreciated that these examples are provided by way of example only and are not intended to limit the scope of the invention.

Example 1

In a 500 ml flask, terephthal carboxyaldehyde g (3.62 g, 27 mmol), an aryl dialdehyde derivative, was dissolved in an alkaline solution comprising calcium hydroxide (3.03 g, 54 mmol) dissolved in water (20 ml) and methanol (150 ml). Once terephthal carboxyaldehyde g was completely dissolved, 2-acetylpyridine D (6.0 ml, 54 mmol), a 2-acetylpyridine derivative, was added and the mixture was stirred at room temperature for 2 days. After the reaction was completed, the resulting precipitate was collected by suction filtration. The solid product was washed with methanol and dried under reduced pressure to give symmetric dienone h (8.09 g, 88% yield).

In a 500 ml flask, the pyridium salt b (7.89 g, 19.5 mmol) and the symmetric dienone h (3.32 g, 9.74 mmol) obtained in Example 1 were added to ammonium acetate (37.5 g, 487 mmol) and dehydrated methanol (250 ml). The mixture was refluxed for 12 hours.

Subsequently, the resulting precipitate was collected by suction filtration and was washed sequentially with water, methanol and acetic acid. The washed product was extracted with boiling toluene and the extract was concentrated. The resulting solid was recrystallized from acetic acid and dried under reduced pressure to give dibromo bis-terpyridine i (1.36 g, 20% yield). These procedures are shown in the following formula (21):

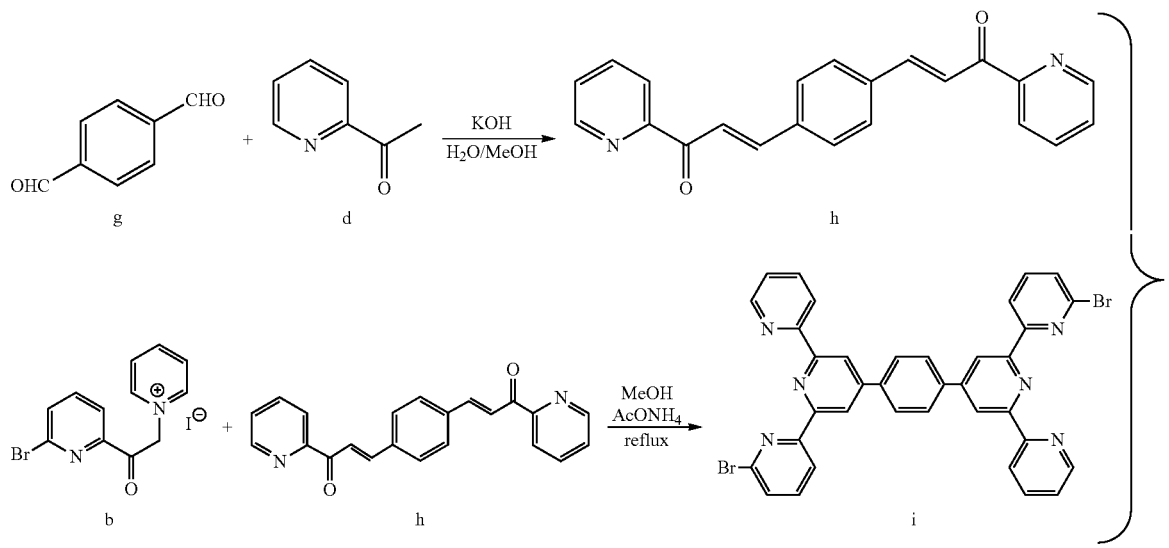

(21)

As in Example 1, the resulting dibromo bis-terpyridine i was identified by NMR spectroscopy. The results are shown below.

$^1$H NMR (CDCl$_3$) δ≅7.35-7.41 (2H, m), 7.52-7.57 (2H, m), 7.71-7.78 (2H, m), 7.86-7.94 (2H, m), 8.05 (4H, s), 8.62-8.68 (4H, m), 8.74-8.78 (4H, m), 8.79-8.83 (2H, m)

The results indicate that the product was the desired dibromo bis-terpyridine.

The dibromo bis-terpyridine i was then subjected to high-resolution mass spectroscopy (HRMS). The results are as follows.

The theoretical value for the molecular formula C$_{36}$H$_{23}$Br$_2$N$_6$ was 679.0345 (M+H$^+$). The found value was 679.0333 (m/z). Since the difference between the theoretical value and the found value was within the range of error, the product was identified to be the dibromo bis-terpyridine of the foregoing molecular formula.

Several embodiments of the second group of the present invention will now be described with reference to FIGS. 3 through 15.

Embodiment 1

Figure 3:
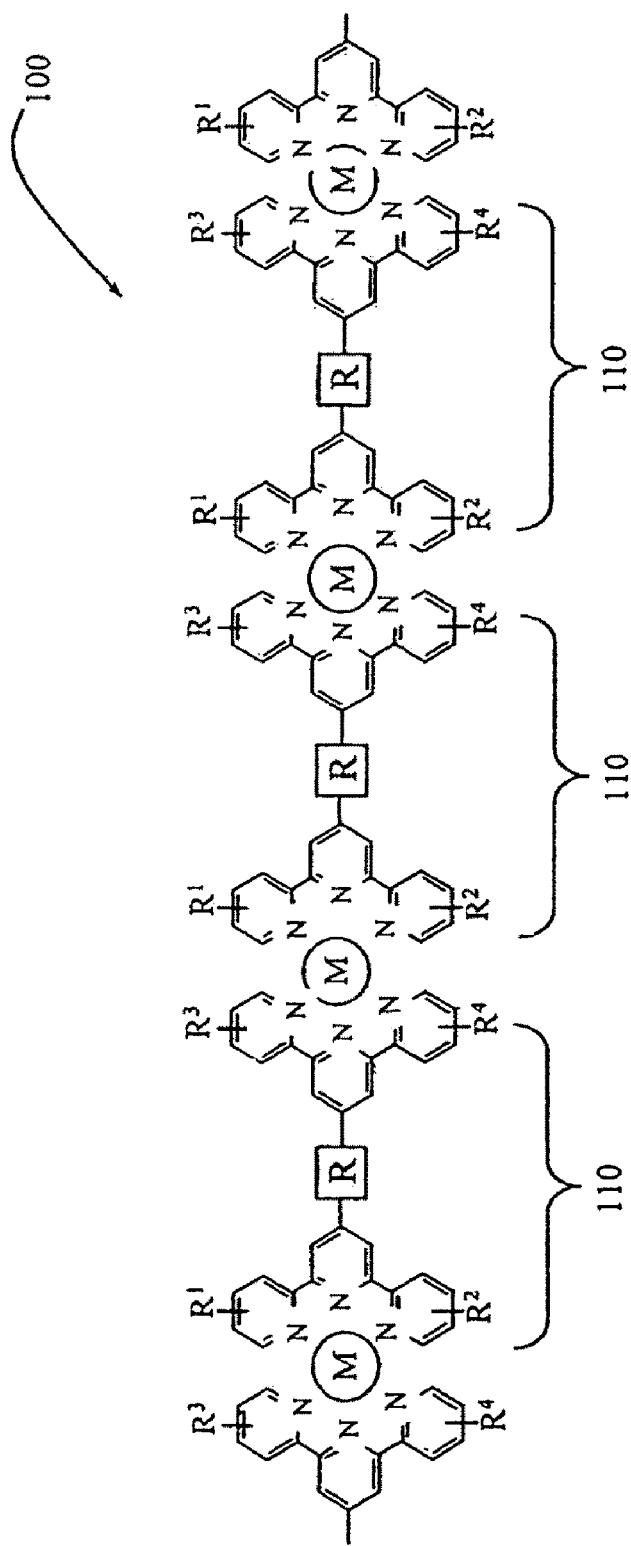
FIG. 3 is a schematic diagram of the polymer material according to Embodiment 1.

FIG. 3 schematically shows a polymer material according to Embodiment 1 of the second group of the present invention.

As shown by the formula (22) below, the polymer material 100 of the present invention includes a bis-terpyridine derivative that serves as a ligand, a metal ion and a counter anion. The formula (22) shows a repeating unit 110:

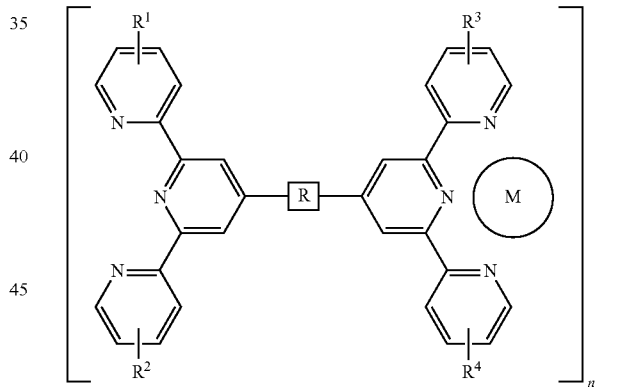

(22)

where M is a metal ion; R is a spacer that contains a carbon atom or a hydrogen atom, or directly links the terpyridyl groups to each other; R$^1$, R$^2$, R$^3$ and R$^4$ are each independently a hydrogen atom, an aryl group or an alkyl group; and n is an integer of 2 or greater indicating the degree of polymerization.

The metal ion is selected from the group consisting of iron ion, cobalt ion, nickel ion and zinc ion. Not only can these ions change their valency upon oxidation/reduction, but they also have different oxidation/reduction potentials in the polymer material 100.

The spacer R may be an aryl group or an alkyl group. In this manner, the angle of the terpyridyl group in the polymer material 100 can be adjusted as desired, making it possible to design the polymer material 100. The aryl group or alkyl group may further contain an oxygen atom or a sulfur atom.

Oxygen atom and sulfur atom are advantageous in designing the polymer material 100 because of their modification property.

The aryl group is preferably an aryl group selected from the group consisting of the formulas (3) through (6) below. Such an aryl group structurally defines the skeleton of the ligand and makes it rigid, so that the polymer material becomes more suitable to make polymer thin film.

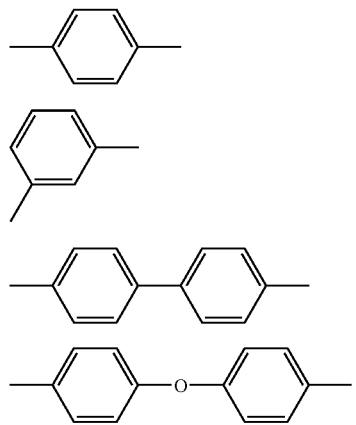

The counter anion is selected from the group consisting of acetate ion, tetrafluoroborate ion, polyoxometalate and combinations thereof. Such a counter anion compensates for the charge of the metal ion and makes the polymer material 100 electrically neutral.

When $R^1$, $R^2$, $R^3$ and $R^4$ are each an aryl group or an alkyl group other than hydrogen atom, examples of such aryl group and alkyl group include, but are not limited to, methyl group, ethyl group, n-butyl group, t-butyl group, phenyl group and tolyl group. The aryl or alkyl group may include additional substituents, including alkyl groups, such as methyl group, ethyl group and hexyl group, alkoxy groups, such as methoxy group and butoxy group, and halogen groups, such as chlorine and bromine.

The polymer material 100 exhibits colors such as blue and red as electrons are transferred between the ligand and the metal ion. A desired color can be achieved by a proper combination of a ligand and a metal ion since the speed of charge transfer varies depending on the combination of ligand and metal ion. The speed of charge transfer may also be controlled by changing the counter anion.

Specifically, the polymer material exhibits blue or purple color by selecting iron ion as the metal ion and acetate ion as the counter anion. The blue or purple color of the polymer turns deep blue (indigo) by replacing the acetate ion with polyoxometalate. The polymer becomes reddish brown by selecting cobalt ion as the metal ion and acetate ion as the counter anion. By replacing the acetate ion with polyoxometalate, the polymer turns from reddish brown to blue. Since these color changes are dependent upon the speed of charge transfer, it is desirable to know the speed of charge transfer for different combinations of metal ion and counter anion beforehand.

The present inventors have found that controlling the electrical potential of the polymer material 100 can change the valency of the metal ion and cause oxidation/reduction reactions (thereby causing the polymer material 100 to exhibit its electrochromic properties). This in turn changes the speed of charge transfer between the ligand and the metal ion and thus brings the polymer material 100 from its colored state into its colorless state. In particular, when the counter anion is polyoxometalate, the polymer material can be readily switched between the colored state and the colorless state since the potential difference required for oxidation/reduction reactions can be made large.

Since the polymer material 100 is a polymer electrolyte that can dissolve into water, methanol and other solvents, it can be further processed after its synthesis.

A process for producing the polymer material 100 of the present invention will now be described step by step.

Step S110: A bis-terpyridine derivative of the formula (24) and a metal salt are refluxed in acetic acid and methanol.

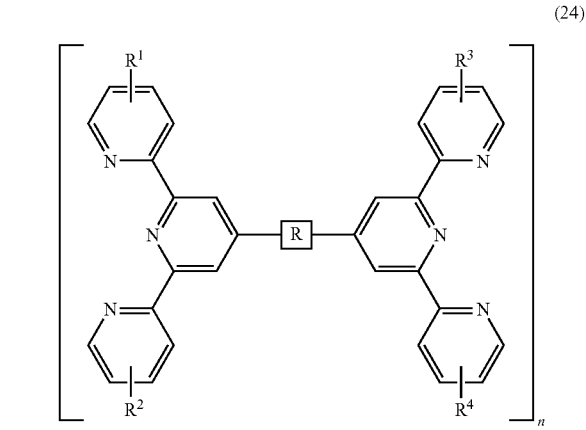

In the above formula, R is a spacer that contains a carbon atom or a hydrogen atom, or directly links the terpyridyl groups to each other; $R^1$, $R^2$, $R^3$ and 4 are each independently a hydrogen atom, an aryl group or an alkyl group; and n is an integer of 2 or greater indicating the degree of polymerization.

The spacer R may be an aryl group or an alkyl group. The aryl group or alkyl group may further contain an oxygen atom or a sulfur atom. The aryl group is preferably an aryl group selected from the group consisting of the formulas (3) through (6) below. Such an aryl group makes the polymer material more suitable to make polymer thin film.

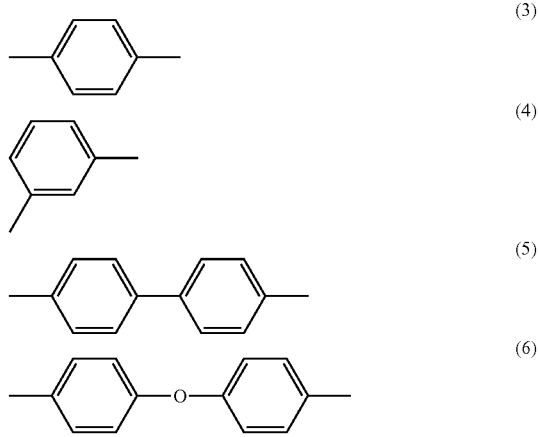

When $R^1$, $R^2$, $R^3$ and $R^4$ are each an aryl group or an alkyl group other than hydrogen atom, examples of such aryl group and alkyl group include, but are not limited to, methyl group, ethyl group, n-butyl group, t-butyl group, phenyl group and tolyl group. The aryl group or alkyl group may include additional substituents, including alkyl groups, such as methyl group, ethyl group and hexyl group, alkoxy groups, such as methoxy group and butoxy group, and halogen groups, such as chlorine and bromine.

The metal salt comprises a combination of a metal ion, which is selected from the group consisting of iron ion, cobalt ion, nickel ion and zinc ion, and a counter anion, which is selected from the group consisting of acetate ion, tetrafluoroborate ion, polyoxometalate and combinations thereof.

In Step S110, acetic acid and methanol serve as solvents for the bis-terpyridine derivative and the metal salt, respectively. While the reflux may be carried out at a temperature of 150° C. for 24 hours, it may be carried out under other conditions. Although the conditions for the reflux vary depending on the spacer and the metal salt selected, those skilled in the art will readily be able to determine such conditions.

Subsequent to Step S110, the mixture resulting from the reflux may be heated to evaporate the solvents and thus form a powder. This powder is colored, for example, purple and is in its reduced state. Such powder can readily dissolve in methanol and is easy to handle.

Embodiment 2

Although Embodiment 1 concerns the case in which the polymer material 100 contains a single species of metal ion, the number of metal ion species used in the polymer material is not limited according to the present invention. In Embodiment 2, a polymer material containing two or more different metal ion species is described.

Figure 4:
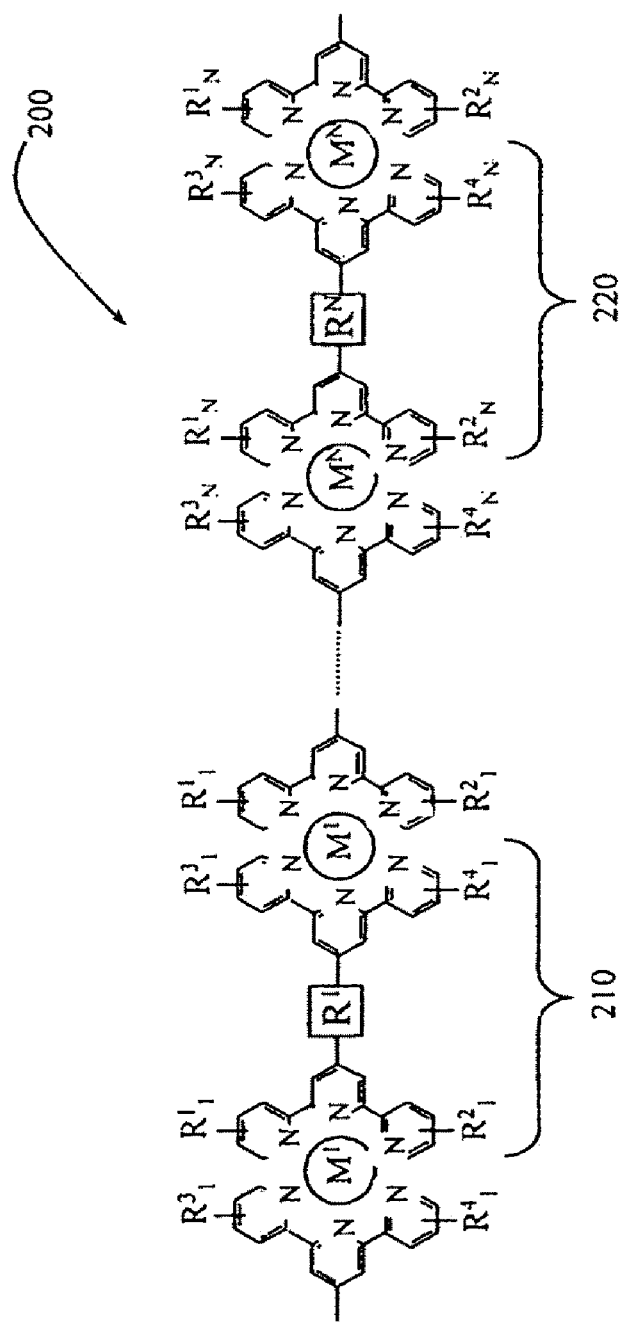
FIG. 4 is a schematic diagram of the polymer material according to Embodiment 2.

FIG. 4 schematically shows a polymer material of Embodiment 2.

As shown by the formula (23) below, the polymer material 200 of the present invention includes a bis-terpyridine derivative that serves as a ligand, a first to Nth metal ions, and a first to Nth counter anions (where N is an integer of 2 or greater).

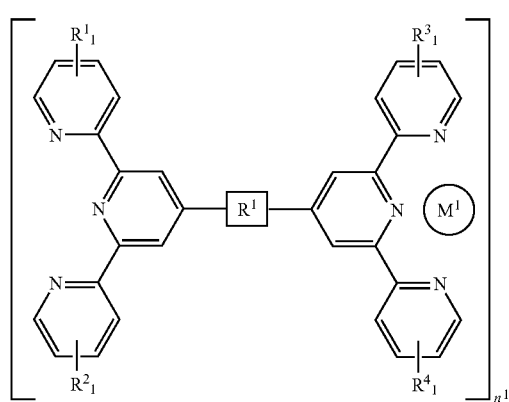

(23)

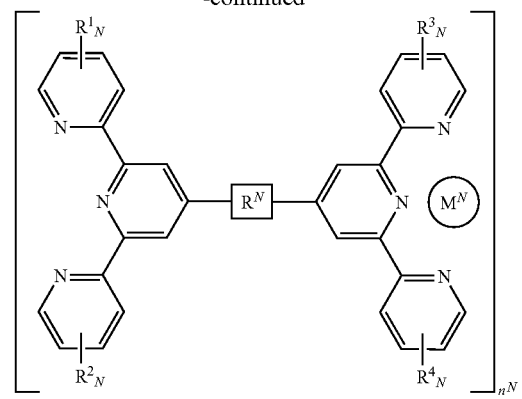

In FIG. 4, a unit 210 includes a bis-terpyridine derivative, a first metal ion $M^1$ and a first counter anion, and a unit 220 includes a bis-terpyridine derivative, an Nth metal ion $M^N$ and an Nth counter anion. In the polymer material 200, the unit 210 and the unit 220 are each polymerized to a degree of polymerization of at least 2.

In the formula (24), $M^1, \ldots, M^N$ are first to Nth different metal ions, respectively (N is an integer of 2 or greater). $R^1, \ldots, R^N$ are each independently a spacer that contains a carbon atom or a hydrogen atom, or directly links corresponding terpyridyl groups to each other (N is an integer of 2 or greater). $R^1_1, \ldots, R^1_N, R^2_1, \ldots, R^2_N, R^3_1, \ldots, R^3_N$, and $R^4_1, \ldots, R^4_N$ are each independently a hydrogen atom, an aryl group or an alkyl group (N is an integer of 2 or greater). $n^1, \ldots, n^N$ are each an integer of 2 or greater indicating the degree of polymerization. First to Nth counter anions may be identical to, different from, or partly identical to one another.

The first to Nth metal ions are each selected from the group consisting of iron ion, cobalt ion, nickel ion and zinc ion. Since electrical charge is transferred at different speeds between the ligand and the different metal ions, these metal ions can cause different colors.

Thus, by combining different metal ions that can cause different colors, the polymer material 200 can be obtained in different colors. It should be appreciated that the first to the Nth metal ions are not limited to the foregoing metal ions, but may be any combination of metal ions that have different speeds of charge transfer.

These metal ions also have different oxidation/reduction potentials, so that a single polymer material 200 can be readily switched between different colored states and the respective colorless states by controlling the electrical potential applied to it.

The spacers $R^1, \ldots, R^N$ are each an aryl group or an alkyl group. The aryl group or alkyl group may further contain an oxygen atom or a sulfur atom. As in Embodiment 1, the aryl group is preferably an aryl group selected from the group consisting of the formulas (3) through (6) below. Such an aryl group structurally defines the skeleton of the ligand and makes it rigid, so that the polymer material becomes more suitable to make polymer thin film.

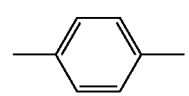

(3)

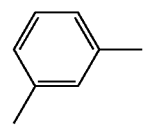

(4)

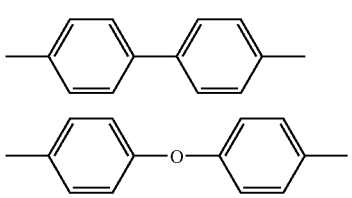
(5)

(6)

The first to the Nth counter anions are each selected from the group consisting of acetate ion, tetrafluoroborate ion, polyoxometalate and combinations thereof. Such a counter anion compensates for the charge of the metal ion and makes the polymer material 200 electrically neutral.

When $R^1_1, \ldots, R^1_N, R^2_1, \ldots, R^2_N, R^3_1, \ldots, R^3_N, R^4_1, \ldots, R^4_N$ are each an aryl group or an alkyl group other than hydrogen atom, examples of such aryl group and alkyl group include, but are not limited to, methyl group, ethyl group, n-butyl group, t-butyl group, phenyl group and tolyl group. The aryl group or alkyl group may include additional substituents, including alkyl groups, such as methyl group, ethyl group and hexyl group, alkoxy groups, such as methoxy group and butoxy group, and halogen groups, such as chlorine and bromine.

As described above, the polymer material 200 includes the unit 210 that is polymerized to a degree of polymerization of 2 or more and the unit 220 that is also polymerized to a degree of polymerization of 2 or more. Since the polymer material 200 contains different metal ions, it can exhibit different colors based on different speeds of charge transfer between the metal ions and the ligand. Also, since the metal ions have different oxidation/reduction potentials, the polymer material 200 can exhibit a specific color based on a specific metal ion by controlling the electrical potential applied to the polymer material. Thus, the polymer material 200, a single material that can exhibit multiple colors, helps reduce the time and cost required in the production of various devices. The polymer material 200 is also a polymer electrolyte that can dissolve into water, methanol and other solvents and can therefore be further processed after its synthesis.

A process for producing the polymer material 200 of the present invention will now be described step by step.

Step S210: Each of first to Nth bis-terpyridine derivatives of the formula (25) (N is an integer of 2 or greater) and each of first to Nth metal salts (N is an integer of 2 or greater) are refluxed in acetic acid and methanol.

(25)

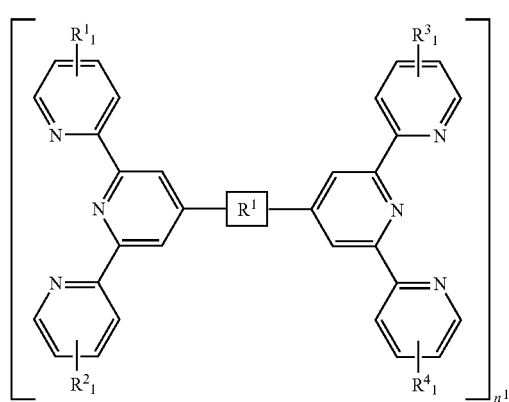

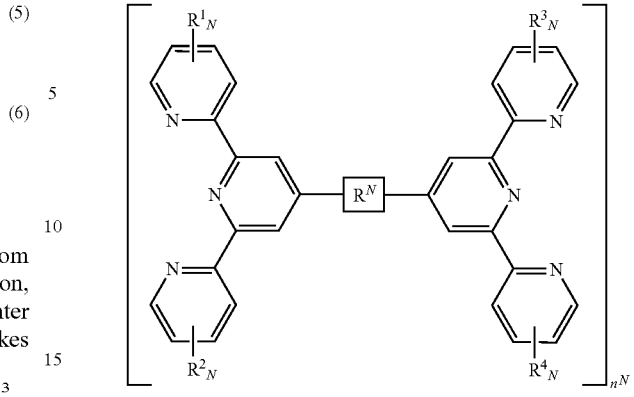

In the above formula, $R^1, \ldots, R^N$ are each independently a spacer that contains a carbon atom or a hydrogen atom, or directly links the terpyridyl groups to each other (N is an integer of 2 or greater). $R^1_1, \ldots, R^1_N, R^2_1, \ldots, R^2_N, R^3_1, \ldots, R^3_N,$ and $R^4_1, \ldots, R^4_N$ are each independently a hydrogen atom, an aryl group or an alkyl group (N is an integer of 2 or greater). $n^1, \ldots, n^N$ is each independently an integer of 2 or greater indicating the degree of polymerization.

The spacers $R^1, \ldots, R^N$ are each an aryl group or an alkyl group. The aryl group or alkyl group may further contain an oxygen atom or a sulfur atom. As in Embodiment 1, the aryl group is preferably an aryl group selected from the group consisting of the formulas (3) through (6) below. Such an aryl group structurally defines the skeleton of the ligand and makes it rigid, so that the polymer material becomes more suitable to make polymer thin film.

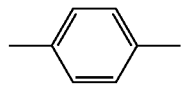
(3)

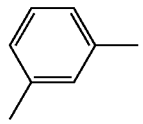
(4)

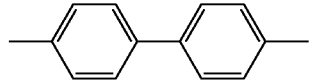
(5)

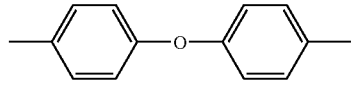
(6)

When $R^1_1, \ldots, R^1_N, R^2_1, \ldots, R^2_N, R^3_1, \ldots, R^3_N, R^4_1, \ldots, R^4_N$ are each an aryl group or an alkyl group other than hydrogen atom, examples of such aryl group and alkyl group include, but are not limited to, methyl group, ethyl group, n-butyl group, t-butyl group, phenyl group and tolyl group. The aryl group or alkyl group may include additional substituents, including alkyl groups, such as methyl group, ethyl group and hexyl group, alkoxy groups, such as methoxy group and butoxy group, and halogen groups, such as chlorine and bromine.

Each of the first to the Nth metal salts comprises a combination of a metal ion, which is selected from the group consisting of iron ion, cobalt ion, nickel ion and zinc ion, and a counter anion, which is selected from the group consisting of acetate ion, tetrafluoroborate ion, polyoxometalate and combinations thereof.

In Step S210, acetic acid and methanol serve as solvents for the bis-terpyridine derivative and the metal salts, respectively, as in Step S110 of Embodiment 1. While the reflux may be carried out at a temperature of 150° C. for 24 hours, it may be carried out under other conditions. Although the conditions for the reflux vary depending on the spacer and the metal salt selected, those skilled in the art will readily be able to determine such conditions.

Step S220: The first to the Nth reaction products obtained in Step S210 are mixed together. The mixing is carried out by stirring the mixture at room temperature for at least 2 hours. The first to the Nth reaction products may be mixed in different proportions or in equal amounts. As one might expect, the color strength of a specific color can be changed by varying the amounts of the reaction products mixed. As shown in FIG. 2, the mixing causes the multiple units 210 and the multiple units 220 to bind to one another in a self-aligning manner.

Subsequent to Step S220, the resulting mixture may be heated to evaporate the solvents and thus form a powder. This powder may have a mixed color of multiple colors caused by the metal ions in their reduced state.

The polymer material 200 can be produced in the same manner as in Step S110 of Embodiment 1, except that the metal salts formed with two or more metal ion species are used. When multiple metal salts are used as starting materials, the polymer is formed during the reflux so that same species of metal ions are arranged in sequence in a self-aligning manner.

Embodiment 3

Electrochromic devices using the polymer materials 100, 200 obtained in Embodiments 1, 2 will now be described.

Figure 5:
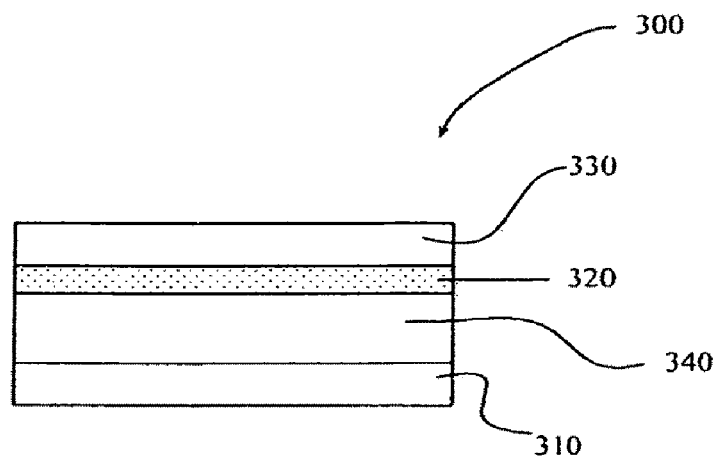
FIG. 5 is a schematic diagram of an electrochromic device according to Embodiment 3.

FIG. 5 schematically shows an electrochromic device according to Embodiment 3.

The electrochromic device 300 includes a first transparent electrode 310, a polymer material 320 arranged on the first transparent electrode 310 and a second transparent electrode 330 arranged on the polymer material 320. The electrochromic device 300 may further include a polymer solid electrolyte 340 arranged between the first transparent electrode 310 and the polymer material 320.

While the first transparent electrode 310 and the second transparent electrode 330 may be any transparent conductive film, they are preferably each an $SnO_2$ film, $In_2O_3$ film or an ITO film formed of a mixture of $In_2O_3$ and $SnO_2$. The first transparent electrode 310 and the second transparent electrode 330 may be deposited on a transparent substrate, such as a glass substrate, by using any physical or chemical vapor deposition technique.

The polymer material 320 is the polymer material 100 or 200 described in Embodiment 1 or 2. The polymer material 320 can be applied on the first transparent electrode 310 by spin coating, dip coating or other coating techniques.

The polymer solid electrolyte 340 is formed by dissolving an electrolyte in a polymer matrix and may contain coloring agents to enhance its contrast. The coloring agents are not added when the enhancement of contrast is not required.

The operation of the electrochromic device 300 is now described.

The first transparent electrode 310 and the second transparent electrode 330 are each connected to a power source and apply a predetermined voltage to the polymer material 320 and the polymer solid electrolyte 340. In this manner, the oxidation/reduction of the polymer material 320 can be controlled.

When the polymer material 320 comprises single polymer material 100 of Embodiment 1, the polymer material 100 can be switched between its colored state and colorless state by controlling oxidation/reduction of the metal ions in the polymer material 100. When the polymer material 320 comprises multiple polymer materials 100 of Embodiment 1, the multiple polymer materials 100 can be individually switched between their colored state and colorless state by individually controlling the electrical potential applied to the multiple polymer materials 100.

When the polymer material 320 comprises polymer material 200 of Embodiment 2, the polymer material 200 can be switched between its colored state and colorless state by individually controlling oxidation/reduction of the multiple metal ions in the polymer material 200. The polymer material 200 of Embodiment 2 is simpler than the multiple polymer materials 100 of Embodiment 1 for use as the polymer material 320 since it can be applied in a single coating operation. Multiple devices 300 may be arranged in a matrix pattern.

The second group of the present invention will now be described with reference to Examples 2 and 5, which are not intended to limit the scope of the present invention.

Example 2

In a 100 ml two-necked flask, 1,4-bis-terpyridine benzene (30 mg, 0.054 mmol), a ligand, was dissolved in 25 ml acetic acid by heating the solution. A solution of iron acetate (9.39 mg, 0.054 mol), a metal salt, in 5 ml methanol was then added to the two-necked flask. The mixture was refluxed at 150° C. for 24 hours in a nitrogen atmosphere.

Subsequently, the reaction mixture in the two-necked flask was transferred to a Petri dish and was dried in the atmosphere to obtain a polymer material as a purple powder (the product is referred to as "FeMEPE," hereinafter). The yield of the powder was 90%.

Figure 6:
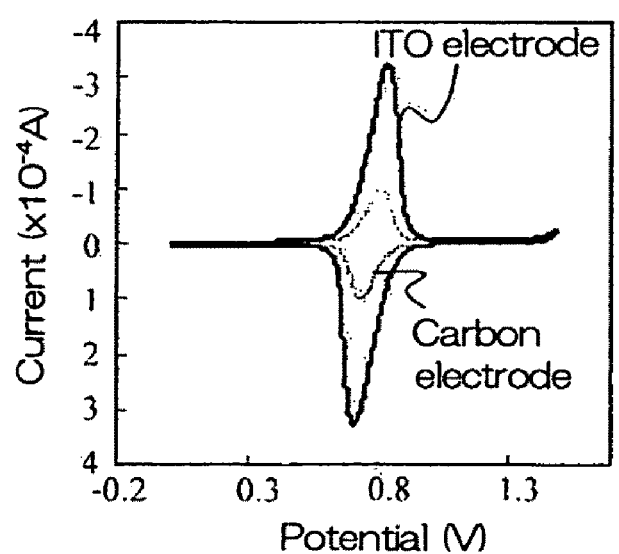
FIG. 6 is a cyclic voltammogram of FeMEPE.

Using a cyclic voltameter CV50W, (BAS, Japan), the electrochemical response of FeMEPE was analyzed. For measurement, working electrodes were prepared by applying a solution of FeMEPE in 20 µl methanol to a glassy carbon electrode (GCE) and an ITO electrode and drying the electrodes. A Pt counter electrode and Ag/Ag+/ACN/TBAP were used as a counter electrode and a reference electrode, respectively. Each electrode was manufactured by BAS. A varying voltage of −0.2 V to 1.5 V was applied and the analysis was performed at a potential scan rate of 0.1 V/s. The results are shown in FIG. 6 and will be described later in detail.

Figure 7:
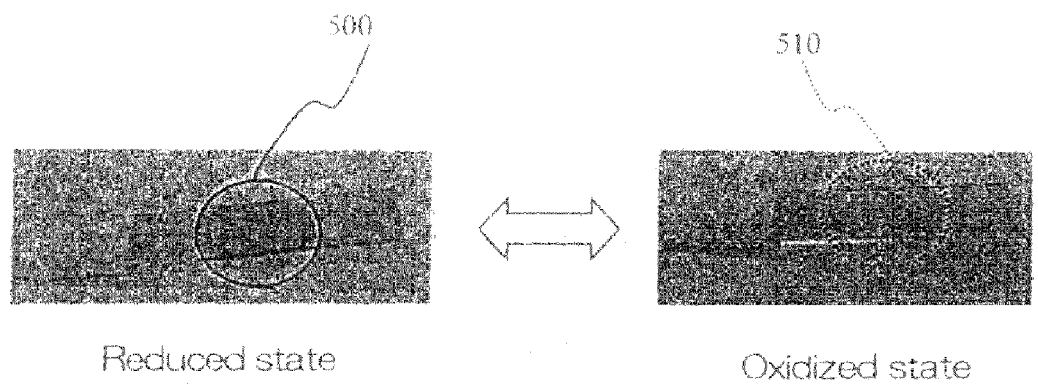
FIG. 7 is a diagram showing color change of FeMEPE.

Next, the color changes of FeMEPE were observed visually. The above-described ITO electrode was used as a sample. Specifically, a voltage was applied to FeMEPE via the ITO film and the changes in color were observed. The results are shown in FIG. 7 and will be described later in detail.

Figure 8:
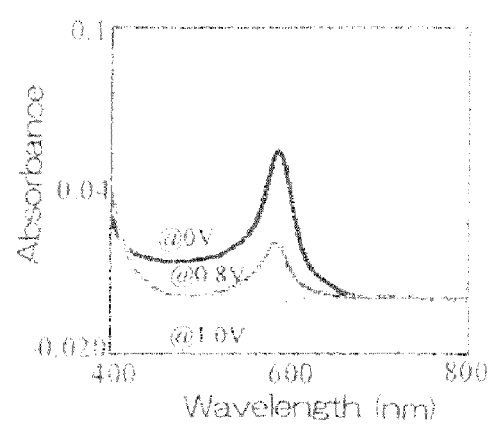
FIG. 8 is absorption spectra of FeMEPE in the UV-visible range.

Next, the sample used in the visual observation was subjected to predetermined voltages (0 V, 0.8 V and 1.0 V) and analyzed for the UV-visible absorption spectrum in the wavelength range of 400 nm to 800 nm using a UV-VIS-NIR spectrometer (UV3150, Shimadzu, Japan) operated in a transmission mode. The results are shown in FIG. 8 and will be described later in detail.

Figure 9:
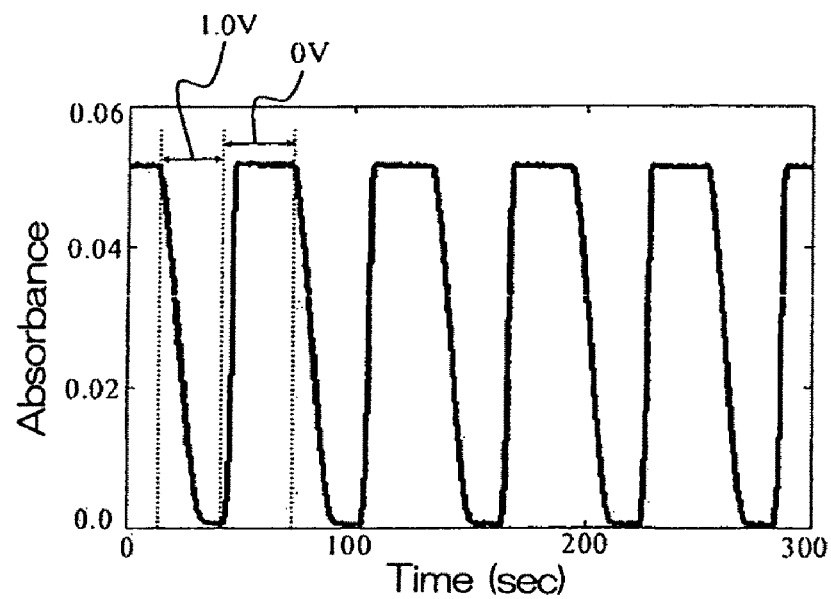
FIG. 9 is a diagram showing the switching characteristic of the peak intensity at a wavelength of 580 nm.

Next, the same sample was analyzed for the speed at which the sample changes between the colored state and the colorless state, as well as for the switching characteristic (electrochromic property). As in the measurement of the UV-visible absorption spectrum, a UV-VIS-NIR spectrometer (UV3150, Shimadzu, Japan) was used to analyze the speed at which the sample changes between the colored state and the colorless state and the changes in the absorption upon development of color by repeatedly applying predetermined voltage cycles (0 V and 1.0 V). The results are shown in FIG. 9 and will be described later in detail.

Example 3

The same procedure was followed as in Example 1, except that cobalt acetate (9.56 mg, 0.054 mmol) was used as the metal salt. The rest of the procedure is the same as in Example 1 and the same description will not be repeated here. The resulting polymer material is referred to as "CoMEPE," hereinafter.

Figure 10:
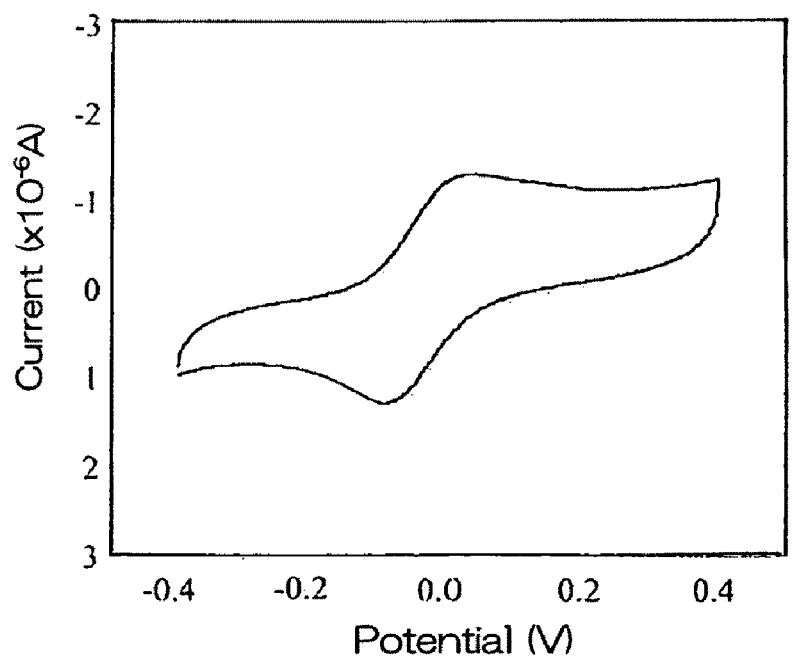
FIG. 10 is a cyclic voltammogram of CoMEPE.

As in Example 2, the electrochemical response of CoMEPE was analyzed. A varying voltage of −0.7 V to 0.8 V was applied and the analysis was performed at a potential scan rate of 0.1 V/s. The results are shown in FIG. 10 and will be described later in detail.

Figure 11:
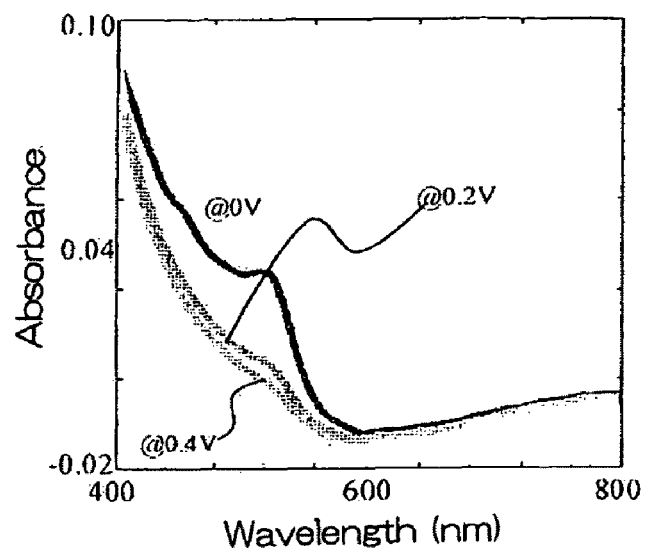
FIG. 11 is absorption spectra of CoMEPE in the UV-visible range.
Figure 12:
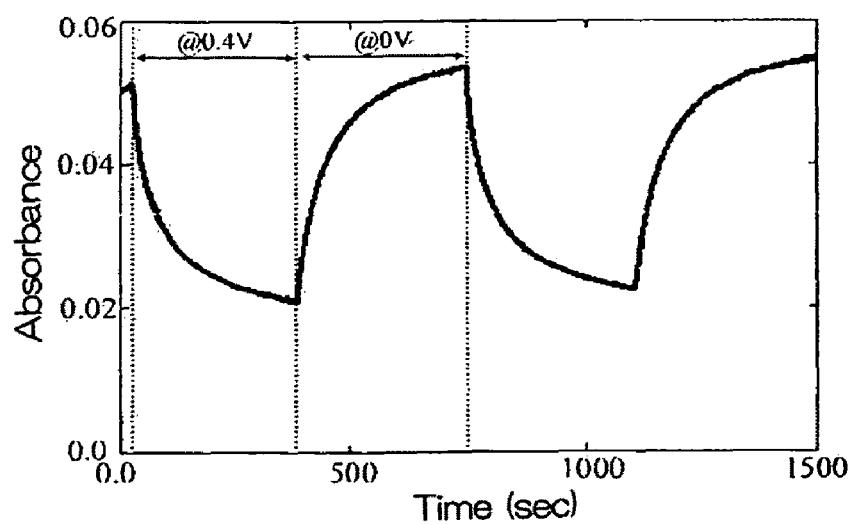
FIG. 12 is a diagram showing the switching characteristic of the peak intensity at a wavelength of 520 nm.

As in Example 2, the CoMEPE sample was subjected to predetermined voltages (0 V, 0.2 V and 0.4 V) and analyzed for the absorption spectrum in the UV-visible range. The speed at which the sample changes between the colored state and the colorless state as well as the switching characteristic were then analyzed by repeatedly applying predetermined voltage cycles (0 V and 0.4 V) to the CoMEPE sample. The results are shown in FIGS. 11 and 12 and will be described later in detail.

Example 4

A solution of FeMEPE (0.5 mg) obtained in Example 1 in methanol (250 μl) was mixed with a solution of CoMEPE (0.5 mg) obtained in Example 2 in methanol (250 μl). Specifically, the mixture was stirred in a beaker at room temperature for 2 hours. The resulting mixture is referred to as "CoMEPE-FeMEPE," hereinafter.

Figure 13:
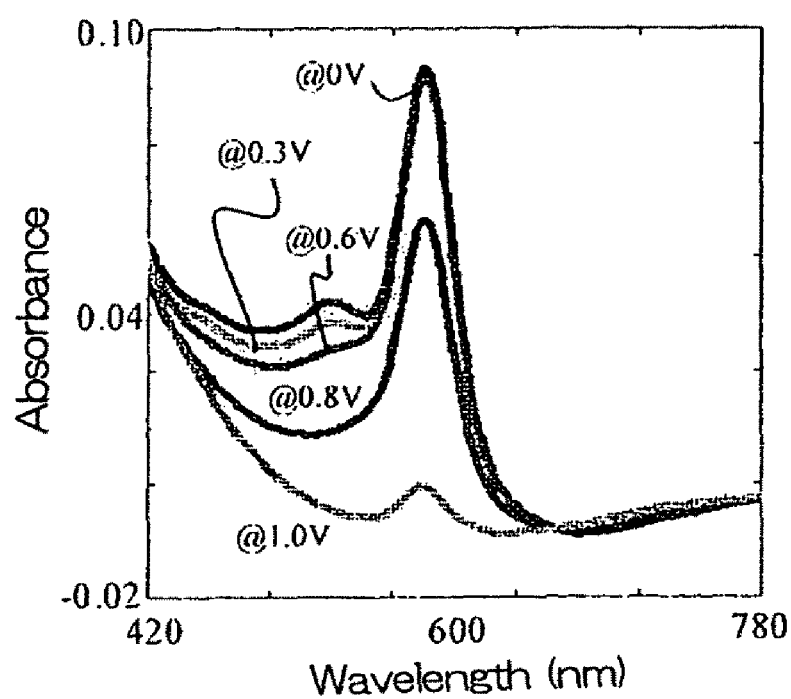
FIG. 13 is absorption spectra of CoMEPE-FeMEPE in the UV-visible range.

As in Examples 2 and 3, the CoMEPE-FeMEPE was subjected to predetermined voltages (0 V, 0.3 V, 0.6 V, 0.8 V and 1.0 V) and analyzed for the UV-visible absorption spectrum in the wavelength range of 420 nm to 780 nm. The results are shown in FIG. 13 and will be described later in detail.

Figure 14:
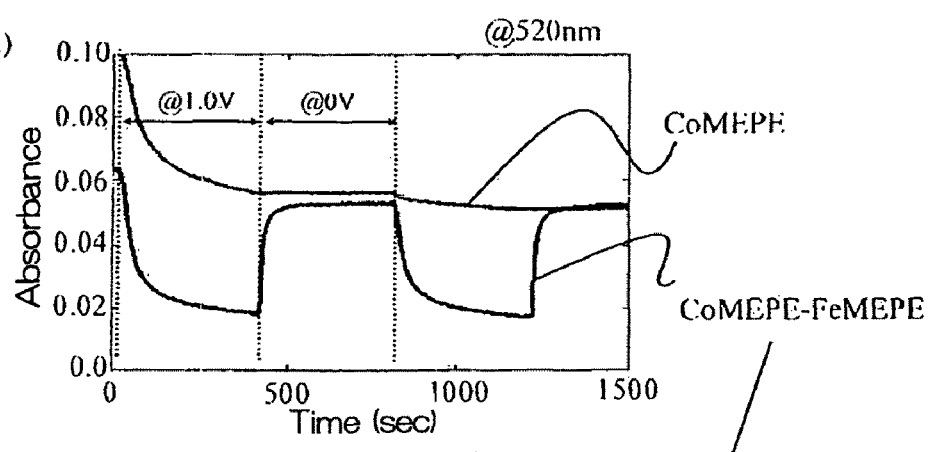
FIG. 14 shows diagrams showing the switching characteristic of the peak intensity at wavelengths of 520 nm and 580 nm, respectively.
Figure 14:
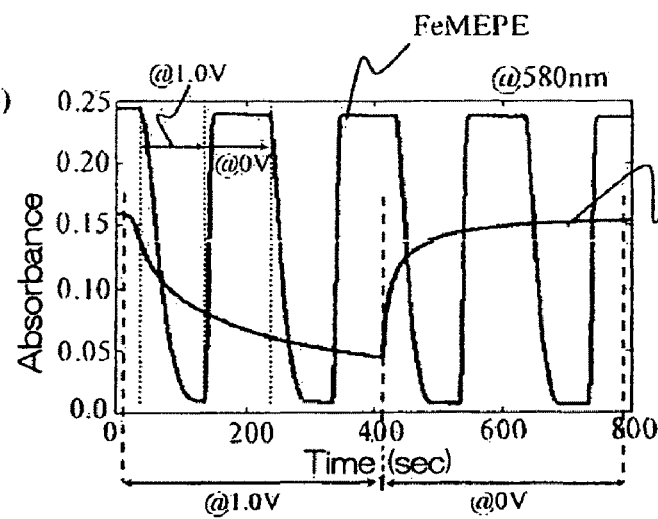

As in Examples 2 and 3, the speed at which the sample changes between the colored state and the colorless state as well as the switching characteristic were then analyzed at absorption wavelengths of 520 nm and 580 nm by repeatedly applying predetermined voltage cycles (0 V and 1.0 V) to the CoMEPE-FeMEPE sample. The results are shown in FIG. 14 and will be described later in detail.

Example 5

In a 100 ml two-necked flask, 1,4-bis-terpyridine benzene (60 mg, 0.108 mmol), a ligand, was dissolved in 50 ml acetic acid by heating the solution. A solution of iron acetate (9.39 mg, 0.054 mol) and cobalt acetate (9.56 mg, 0.054 mol), each a metal salt, in 10 ml methanol was then added to the two-necked flask. The rest of the procedure is the same as in Examples 2 and 3 and the same description will not be repeated here. A reddish purple polymer material was obtained (the product is referred to as "CoMEPE'-FeMEPE'," hereinafter).

Figure 15:
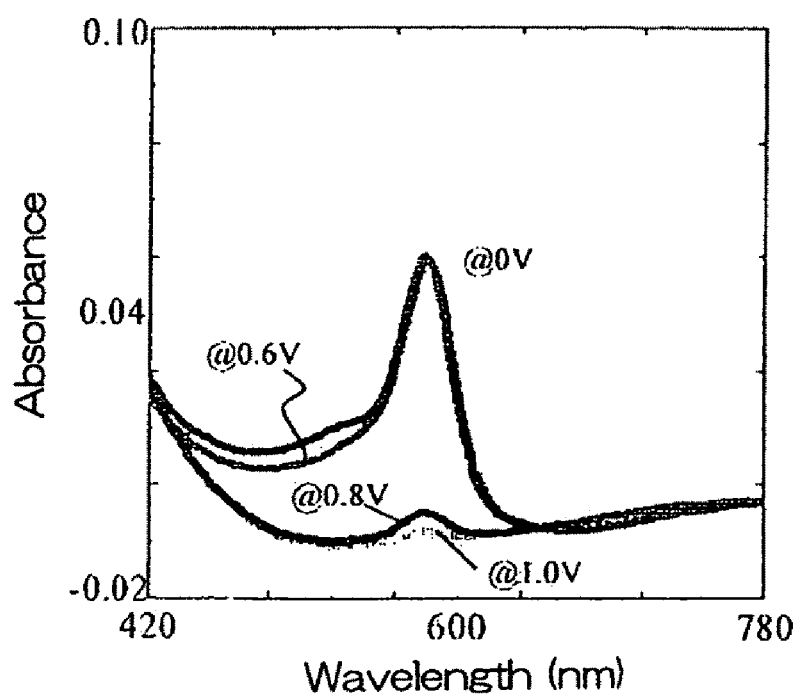
FIG. 15 is absorption spectra of CoMEPE'-FeMEPE' in the UV-visible range.

As in Examples 2 through 4, the CoMEPE'-FeMEPE' was subjected to predetermined voltages (0 V, 0.6 V, 0.8 V and 1.0 V) and analyzed for the UV-visible absorption spectrum in the wavelength range of 420 nm to 780 nm. The results are shown in FIG. 15 and will be described later in detail.

FIG. 6 is a cyclic voltammogram of FeMEPE.

The ITO electrode and the carbon electrode each showed a current peak indicating oxidation/reduction at 0.77 V.

The peak observed when the potential was scanned from −0.2 V to +1.5 V indicates oxidation and the peak observed when the potential was scanned from +1.5 V to −0.2 V indicates reduction. The oxidation occurs as the valency of the iron ion in FeMEPE increases from 2 to 3 whereas the reduction occurs as the valency of the iron ion decreases from 3 to 2.

The peak currents indicating oxidation and reduction had the same value for each electrode, which demonstrates that the oxidation/reduction of FeMEPE takes place in a reversible manner. The difference in the peak current between the ITO electrode and the carbon electrode results from the difference in the electrode size (surface area). The scanning was repeated 500 times, each producing the same result. This suggests that the resulting FeMEPE does not fatigue by application of voltage.

FIG. 7 is a diagram showing the color changes of FeMEPE.

In the reduced state, the region 500 was tinted purple (left in FIG. 7). When the FeMEPE was subjected to a potential scan from 0 V to 1.3 V, oxidation occurred at 0.7 V, causing the region 500 to turn from purple to colorless state (corresponding to region 510) (right in FIG. 7).

When the potential applied to the FeMEPE was again scanned from 1.3 V to 0 V, reduction occurred at 0.7 V, causing the material to turn purple (region 500) (left in FIG. 7). Thus, the coloration and discoloration of FeMEPE was visually confirmed.

FIG. 8 shows absorption spectra of FeMEPE in the UV-visible range.

Based on the results of FIG. 6, voltages of 0 V (reduced state), 0.8 V (oxidation/reduction state) and 1.0 V (oxidized state) were applied. The absorption spectrum at 0 V showed a distinct peak at a wavelength of 580 nm. This peak indicates the purple color of FeMEPE observed in FIG. 7. The purple color results from the speed of charge transfer from $Fe^{2+}$ ion to the ligand in FeMEPE.

The absorption spectrum at 0.8 V also showed a peak at a wavelength of 580 nm, but the peak intensity was lower than that of the absorption spectrum at 0 V. This is because oxidation took place near 0.8 V, as described with reference to FIG. 6. Specifically, when a voltage of 0.8 V is applied to FeMEPE, both $Fe^{2+}$ ion and $Fe^{3+}$ ion are present in FeMEPE. Thus, charge is transferred from $Fe^{2+}$ ion to the ligand at a certain speed, causing the purple color. In the meantime, charge is also transferred from $Fe^{3+}$ ion to the ligand at a certain speed. This causes a decrease in the peak intensity of the purple color.

The absorption spectrum at 1.0 V did not show absorption at a wavelength of 580 nm, indicating that the FeMEPE remained colorless without turning purple. Specifically, when a voltage of 1.0 V is applied, the FeMEPE is in a completely oxidized state in which all iron ions are present in the form of $Fe^{3+}$ ion. Thus, there is no charge transfer from $Fe^{2+}$ ion to the ligand that contributed to the purple color, and thus, no color.

These observations suggest that the peak intensity, or the intensity of the purple color, of FeMEPE can be varied by controlling the voltage (potential) applied to the FeMEPE. The material can be highly practical since it can be controlled by a voltage of about 1 V.

FIG. 9 is a diagram showing the switching characteristic of the peak intensity at a wavelength of 580 nm. The rate constant determined by switching the applied voltage from 0 V to 1.0 V and measuring the time it took before the absorbance at 580 nm reached 0 (colorless state) was $6.5\times10^{-2}$/s. Likewise, the rate constant determined by switching the applied voltage from 1.0 V to 0 V and measuring the time it took before the absorbance at 580 nm reached a predetermined value (colored state) was also $6.5\times10^{-2}$/s.

This observation also indicates that the coloration and discoloration of FeMEPE is a reversible process that takes place in a very short period of time. The speed is comparable to conventional electrochromic materials.

The absorbance at 580 nm (thus, the intensity of the purple color) did not change after the switching of voltage was repeated 500 times, indicating desirable fatigue characteristic.

FIG. 10 is a cyclic voltammogram of CoMEPE.

In FIG. 8, CoMEPE was applied to an ITO electrode. Unlike FeMEPE, a current peak indicating oxidation/reduction was observed at 0.20 V. The peak observed when the potential was scanned from −0.5 V to +0.3 V indicates oxidation and the peak observed when the potential was scanned from +0.3 V to −0.5 V indicates reduction. As is the case with FeMEPE, the oxidation occurs as the valency of the cobalt ion in CoMEPE increases from 2 to 3 whereas the reduction occurs as the valency of the cobalt ion decreases from 3 to 2.

The peak currents indicating oxidation and reduction had the same value for each electrode, which demonstrates that, like FeMEPE, the oxidation/reduction of CoMEPE also takes place in a reversible manner. It was visually confirmed that CoMEPE was tinted reddish brown in the reduced state and was colorless in the oxidized state.

FIG. 11 shows absorption spectra of CoMEPE in the UV-visible range.

Based on the results of FIG. 10, voltages of 0 V (reduced state), 0.2 V (oxidation/reduction state) and 0.4 V (oxidized state) were applied. The absorption spectrum at 0 V showed a distinct peak at a wavelength of 520 nm. This peak indicates the visually observed reddish brown color of CoMEPE. The reddish brown color results from the speed of charge transfer from $Co^{2+}$ ion to the ligand in CoMEPE.

The absorption spectrum at 0.2 V also showed a peak at a wavelength of 520 nm, which was weaker than that of the absorption spectrum at 0 V. This is because oxidation took place near 0.2 V. Specifically, when a voltage of 0.2 V is applied to CoMEPE, both $Co^{2+}$ ion and $Co^{3+}$ ion are present in CoMEPE. Thus, charge is transferred from $Co^{2+}$ ion to the ligand at a certain speed, causing the reddish brown color. In the meantime, charge is also transferred from $Co^{3+}$ ion to the ligand at a certain speed. This causes a decrease in the peak intensity of the reddish brown color.

The peak intensity of CoMEPE upon oxidation/reduction (at 0.2 V) is lower than the peak intensity of FeMEPE upon oxidation/reduction (at 0.8 V) described in Example 2 because the color developed by CoMEPE is fainter than the color developed by FeMEPE.

The absorption spectrum at 0.4 V did not show absorption at a wavelength of 520 nm, indicating that the CoMEPE remained colorless without turning reddish brown. Specifically, when a voltage of 0.4 V is applied, the CoMEPE is in a completely oxidized state in which all cobalt ions are present in the form of $Co^{3+}$ ion. Thus, there is no charge transfer from $Co^{2+}$ ion to the ligand that contributed to the reddish brown color, and thus, no color.

These observations suggest that the peak intensity, or the intensity of the reddish brown color, of CoMEPE can be varied by controlling the voltage (potential) applied to the CoMEPE. In addition, a device that exhibits different colors can be readily constructed by combining single layers of CoMEPE and FeMEPE because of the difference in the oxidation/reduction potential between FeMEPE and CoMEPE.

FIG. 12 is a diagram showing the switching characteristic of the peak intensity at a wavelength of 520 nm. The rate constant determined by switching the applied voltage from 0 V to 0.4 V and measuring the time it took before the absorbance at a wavelength of 520 nm reached 0 was $2.0\times10^{-2}$/s. Likewise, the rate constant determined by switching the applied voltage from 0.4 V to 0 V and measuring the time it took before the absorbance at a wavelength of 520 nm reached a predetermined value was also $2.0\times10^{-2}$/s.

This observation indicates that CoMEPE changes between its colored state and colorless state at a slower speed than does FeMEPE and there is a margin for improvement in that respect. Nonetheless, that the reversible coloration/discoloration of CoMEPE can occur at an oxidation/reduction potential different from that that causes the color changes of FeMEPE can be advantageous in designing devices.

The absorbance at 520 nm (thus, the intensity of the reddish brown color) did not change after the switching of voltage was repeated multiple times, indicating desirable fatigue characteristic.

FIG. 13 shows absorption spectra of CoMEPE-FeMEPE in the UV-visible range.

The UV-visible absorption spectra of the CoMEPE-FeMEPE were measured by varying the electrical potential of the material from 0 V (both Co and Fe in reduced state), to 0.3 V (Co in oxidation/reduction state, Fe in reduced state), to 0.6 V (Co in oxidized state, Fe in reduced state), to 0.8 V (Co in oxidized state, Fe in oxidation/reduction state), and to 1.0 V (both Co and Fe in oxidized state). It was visually confirmed that CoMEPE-FeMEPE turned sequentially from reddish purple, to bluish purple, to blue, and then to colorless state as the potential was varied.

At 0 V, the CoMEPE-FeMEPE developed a reddish purple color. The absorption spectrum at 0 V showed distinct peaks at wavelengths of 520 nm and 580 nm, which correspond to the peaks of FeMEPE and CoMEPE described with reference to FIGS. 8 and 11, respectively. This demonstrates that Co and Fe are both in their reduced state at this potential. Having peaks at wavelengths of 520 nm (reddish brown) and 580 nm (purple), the CoMEPE-FeMEPE was visually recognized as reddish purple. These observations suggest that the CoMEPE-FeMEPE contains CoMEPE and FeMEPE as they were produced.

At 0.3 V, the CoMEPE-FeMEPE developed a bluish purple color. The absorption spectrum at 0.3 V showed a peak at a wavelength of 520 nm that was weaker than the corresponding peak observed at 0 V. This is because oxidation of Co took place near 0.3 V. On the other hand, the peak intensity at a wavelength of 580 nm was substantially the same as that observed at 0 V. These observations suggest that only Co in the CoMEPE-FeMEPE is oxidized at this potential.

At 0.6 V, the CoMEPE-FeMEPE developed a purple color. The absorption spectrum at 0.6 V had no peak at a wavelength of 520 nm, indicating that all Co ions in the CoMEPE-FeMEPE are present in the form of $Co^{3+}$ ion. On the other hand, the peak intensity at a wavelength of 580 nm was substantially the same as those observed at 0 V and 0.3 V.

At 0.8 V, the CoMEPE-FeMEPE developed a purple color. The absorption spectrum at 0.8 V had no peak at a wavelength of 520 nm, but showed a distinct peak at a wavelength of 580 nm though the peak intensity was lower than those observed in the absorption spectra at 0 V, 0.3 V and 0.6 V. This suggests that oxidation of Fe starts near 0.8 V.

At 1.0 V, the CoMEPE-FeMEPE developed a faint purple color. The absorption spectrum at 1.0 V had no peak at 520 nm and the absorbance at this wavelength became substantially 0. On the other hand, the peak intensity at a wavelength of 580 nm significantly decreased as compared to those observed at 0 V, 0.3 V, 0.6 V and 0.8 V. These observations suggest that 1.0 V corresponds to the oxidation/reduction potential of the CoMEPE-FeMEPE although the oxidation of Fe is not completed even near 1.0 V.

Since the CoMEPE and the FeMEPE have different oxidation/reduction potentials, the composite of CoMEPE and FeMEPE can be switched between a colored state and a colorless state for the tints of reddish brown, purple or a mixed color thereof (reddish purple) as desired by controlling the electrical potential applied to it.

FIG. 14 is a diagram showing the switching characteristic of the peak intensity at wavelengths of 520 nm and 580 nm.

FIG. 14(A) shows the switching characteristic of the peak intensity at a wavelength of 520 nm. The change in the peak intensity at a wavelength of 520 nm was measured by alternately applying 1.0 V and 0 V to the CoMEPE-FeMEPE. For reference, CoMEPE obtained in Example 2 was also analyzed in the same manner and the results are shown together.

The CoMEPE alone underwent insulation breakdown when 1.0 V was applied to it. On the other hand, the composite showed electrochromic behavior without undergoing insulation breakdown when 1.0 V was applied. This is considered to be because Co becomes more stable when present with Fe.

The rate constant determined by switching the applied voltage from 0 V to 1.0 V and measuring the time it took before the absorbance at a wavelength of 520 nm became minimum (colorless state) was $2.0 \times 10^{-2}$/s, as described with reference to FIG. 12. Likewise, the rate constant determined by switching the applied voltage from 1.0 V to 0 V and measuring the time it took before the absorbance at a wavelength of 520 nm reached a predetermined value (colored state) was also $2.0 \times 10^{-2}$/s. This observation indicates that the coloration and discoloration of CoMEPE-FeMEPE is a reversible process and the composite changes between its colored state and colorless state in a similar manner to CoMEPE alone.

The absorbance at a wavelength of 520 nm did not change after the switching of voltage was repeated multiple times, indicating desirable fatigue characteristic.

FIG. 14(B) is a diagram showing the switching characteristic of the peak intensity at a wavelength of 580 nm. For reference, the results of FIG. 9 are shown together. The rate constant determined by switching the applied voltage from 0 V to 1.0 V and measuring the time it took before the absorbance at a wavelength of 580 nm became minimum was $5.0 \times 10^{-3}$/s. The value was 7.7% of the rate constant of FeMEPE alone, indicating that iron is oxidized at a slower rate in the composite. This suggests that the slight peak at a wavelength of 580 nm in the absorption spectrum of the CoMEPE-FeMEPE at 1.0 V (a higher voltage than the oxidation/reduction potential of Fe) shown in FIG. 13 is due to the significantly decreased oxidation rate of iron in CoMEPE-FeMEPE. The reason that the absorbance at a wavelength of 580 nm did not become completely 0 is that the voltage was forcibly switched after 400 seconds. It should be noted that had the voltage been applied for a longer period of time, the absorbance would have become 0.

The absorbance at a wavelength of 580 nm did not change after the switching of voltage was repeated multiple times, indicating desirable fatigue characteristic.

These results demonstrate that the CoMEPE-FeMEPE obtained in Example 4 does not comprise randomly arranged CoMEPE and FeMEPE, but rather is a block copolymer comprising 1,4-bis(terpyridine)benzene, iron and cobalt.

FIG. 15 shows absorption spectra of CoMEPE'-FeMEPE' in the UV-visible range.

The UV-visible absorption spectra of the CoMEPE'-FeMEPE' were measured by varying the electrical potential of the material from 0 V (both Co and Fe in reduced state), to 0.6 V (Co in oxidized state, Fe in reduced state), to 0.8 V (Co in oxidized state, Fe in oxidation/reduction state), and to 1.0 V (both Co and Fe in oxidized state). It was visually confirmed that, similar to the CoMEPE-FeMEPE of Example 3, the CoMEPE'-FeMEPE' turned sequentially from reddish purple, to bluish purple, to purple, and then to colorless state as the potential was varied.

Similar to CoMEPE-FeMEPE, the CoMEPE'-FeMEPE' developed a reddish purple color at 0 V. The absorption spectrum at 0 V showed a distinct peak at a wavelength of 580 nm and a slight broad peak at a wavelength of 520 nm.

The broad peak at a wavelength of 520 nm and the distinct peak at a wavelength of 580 nm correspond to the peaks of FeMEPE and CoMEPE described with reference to FIGS. 8 and 11, respectively. This demonstrates that Co and Fe are both in their reduced state at this potential.

The reason that the peak at 520 nm is broader than the corresponding peaks in FIGS. 11 and 13 is that the proportion of CoMEPE present in the CoMEPE'-FeMEPE' is less than that of FeMEPE.

As in FIG. 13, the CoMEPE'-FeMEPE', which showed peaks at wavelengths of 520 nm (reddish brown) and 580 nm (purple), was visually recognized as reddish purple. These observations suggest that the CoMEPE'-FeMEPE' contains CoMEPE and FeMEPE as they were produced.

At 0.6 V, the CoMEPE'-FeMEPE' developed a purple color. While the absorption spectrum at 0.6 V had no peak at a wavelength of 520 nm, the absorbance did not become completely 0. The reason for this is considered to be that although Co ion in the CoMEPE'-FeMEPE' was oxidized to $Co^{3+}$ ion, the oxidization rate of Co decreased significantly. On the other hand, the peak intensity at a wavelength of 580 nm was substantially the same as that observed at 0 V.

At 0.8 V, the CoMEPE'-FeMEPE' developed a faint blue color. The absorption spectrum at 0.8 V had no peak at a wavelength of 520 nm and the absorbance became 0 at this wavelength. The peak intensity at a wavelength of 580 nm was lower than those observed in the absorption spectra at 0 V and 0.6 V. This suggests that oxidation of Fe starts near 0.8 V.

At 1.0 V, the CoMEPE'-FeMEPE' was colorless. The absorption spectrum at 1.0 V had no peak at a wavelength of 520 nm. The peak at 580 nm was also substantially diminished.

Since the CoMEPE and the FeMEPE have different oxidation/reduction potentials, the composite of CoMEPE and FeMEPE can be switched between a colored state and a colorless state for the tints of reddish brown, purple or a mixed color thereof (reddish purple) as desired by controlling the electrical potential applied to it.

INDUSTRIAL APPLICABILITY

The terpyridine monomer of the present invention has a strong ability to coordinate with metal atoms. Such a monomer enables design of various materials. Specifically, organic polymer-metal composite materials in which the polymer is strongly coordinated with the metal atoms can be readily prepared from the terpyridine monomer of the present invention. Such composite materials can be used in light-emitting devices, energy-converting materials, drug delivery systems, sensors, high-performance catalysts, solar batteries and other technical fields.

In addition, polymer materials obtained by designing a polymer material comprising the terpyridine monomer of the present invention and having a specific composition and deriving the polymer material can be readily switched between a colored state and a colorless state by controlling the electrical potential applied to it. Such polymer materials can be used in display devices, light modulation devices, electronic papers and other technical fields.

The invention claimed is:

1. A linear electrochromic polymer material comprising first to Nth bis-terpyridine derivatives (N is an integer of 2 or greater), first to Nth metal ions (N is an integer of 2 or greater) and first to Nth counter anions (N is an integer of 2 or greater), the electrochromic polymer material being represented by the following formula:

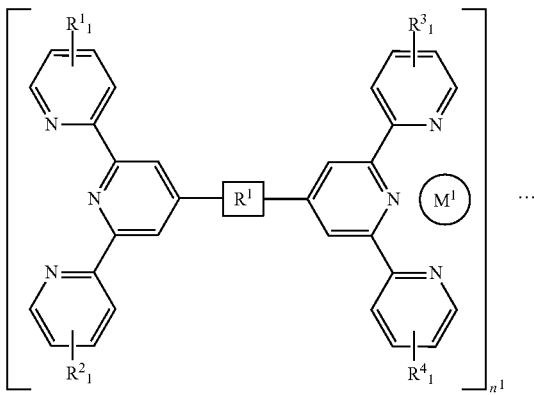

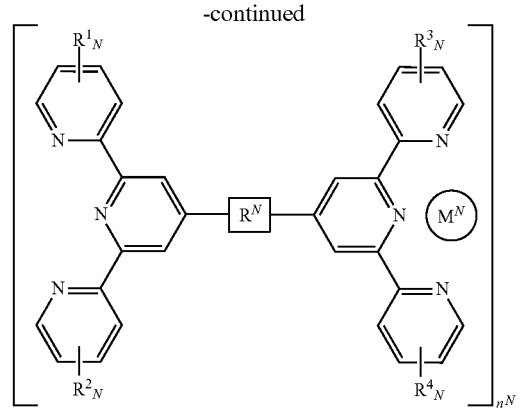

where $M^1, \ldots, M^N$ are first to Nth different metal ions, respectively (N is an integer of 2 or greater); $R^1, \ldots, R^N$ are each independently a spacer that contains a carbon atom or a hydrogen atom, or directly links corresponding terpyridyl groups to each other (N is an integer of 2 or greater); $R^1{}_1, \ldots, R^1{}_N, R^2{}_1, \ldots, R^2{}_N, R^3{}_1, \ldots, R^3{}_N, R^4{}_1, \ldots, R^4{}_N$ are each independently a hydrogen atom, an aryl group or an alkyl group (N is an integer of 2 or greater); $n^1, \ldots, n^N$ are each an integer of 2 or greater indicating the degree of polymerization; and the first to Nth counter anions are identical to, different from, or partly equal to one another.

2. An electrochromic device comprising a first transparent electrode substrate, a second transparent electrode substrate, the polymer material according to claim 1 arranged between the first transparent electrode substrate and the second transparent electrode substrate, and an electrolyte arranged between the first transparent electrode substrate and the polymer material according to claim 1.

* * * * *